(12) United States Patent
Stefanovic

(10) Patent No.: US 8,697,385 B1
(45) Date of Patent: Apr. 15, 2014

(54) PROTEIN CONTROLLING SYNTHESIS OF COLLAGEN AND ASSOCIATED METHODS

(71) Applicant: Florida State University Research Foundation, Inc., Tallahassee, FL (US)

(72) Inventor: Branko Stefanovic, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 13/706,747

(22) Filed: Dec. 6, 2012

Related U.S. Application Data

(63) Continuation of application No. 12/898,849, filed on Oct. 6, 2010.

(60) Provisional application No. 61/248,928, filed on Oct. 6, 2009.

(51) Int. Cl.
*C12Q 1/37* (2006.01)

(52) U.S. Cl.
USPC .......................................................... 435/23

(58) Field of Classification Search
None
See application file for complete search history.

(56) References Cited

PUBLICATIONS

Cai et al., "Coming together: liver fibrosis, collagen mRNAs and the RNA binding protein", Expert Reviews of Gastroenterology & Hepatology, Feb. 2009, vol. 3, No. 1, pp. 1-3.*
Thomas et al., "Targeting RNA with Small Molecules", Chemical Reviews, 2007, vol. 108, No. 4, pp. 1171-1224.*

* cited by examiner

*Primary Examiner* — Suzanne M Noakes
(74) *Attorney, Agent, or Firm* — Allen, Dyer et al.

(57) ABSTRACT

A method of screening an agent for ability to interfere with collagen synthesis includes the steps of reacting a polypeptide having an amino acid sequence comprising SEQ ID NO: 1 with collagen mRNAs in the presence of the agent and detecting if the agent has interfered with binding of the polypeptide to the mRNAs. Another method includes the steps of reacting the polypeptide with nonmuscle myosin filaments in the presence of the agent and detecting if the agent has interfered with binding of the polypeptide to the nonmuscle myosin filaments.

3 Claims, 14 Drawing Sheets
(3 of 14 Drawing Sheet(s) Filed in Color)

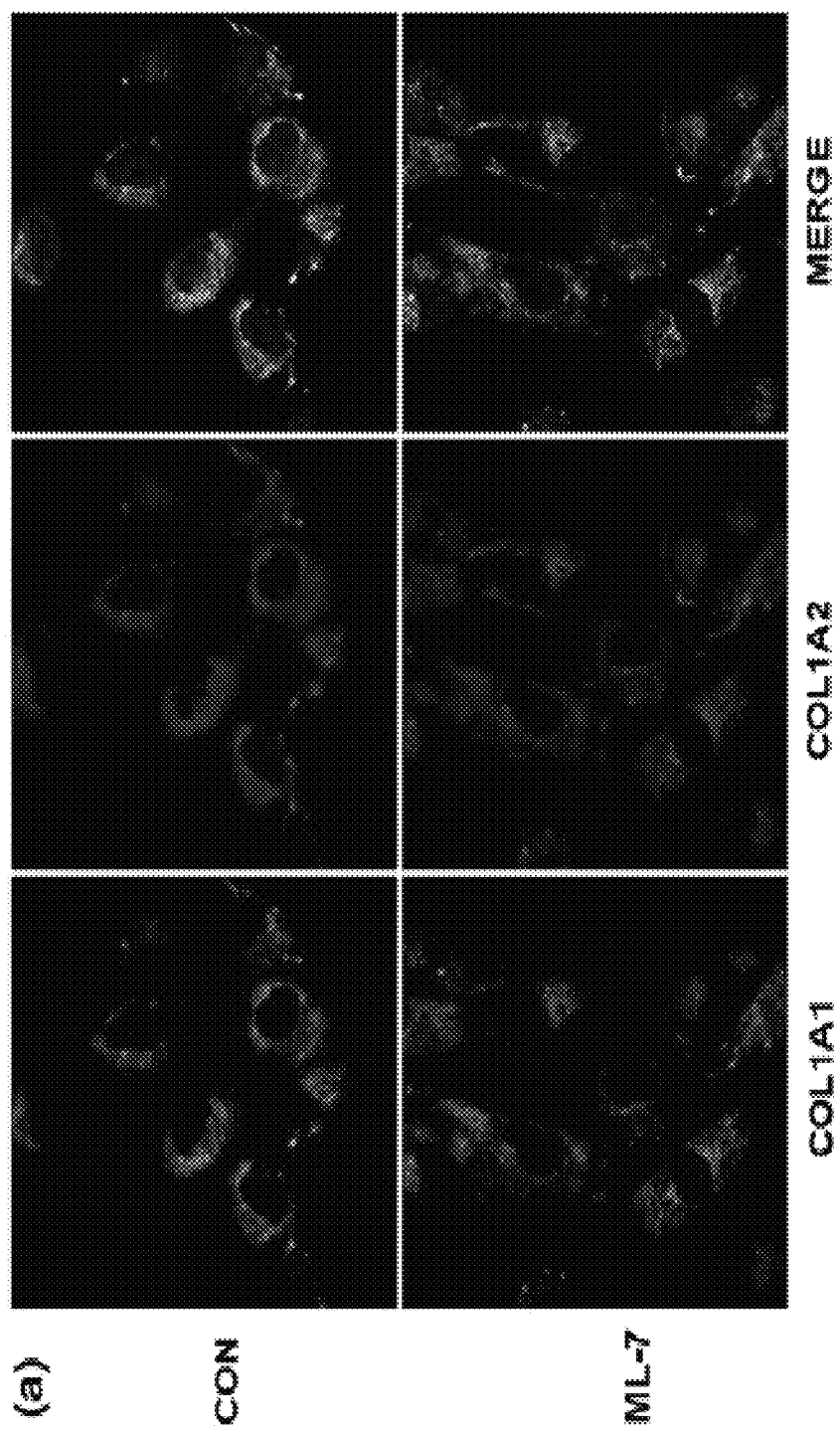

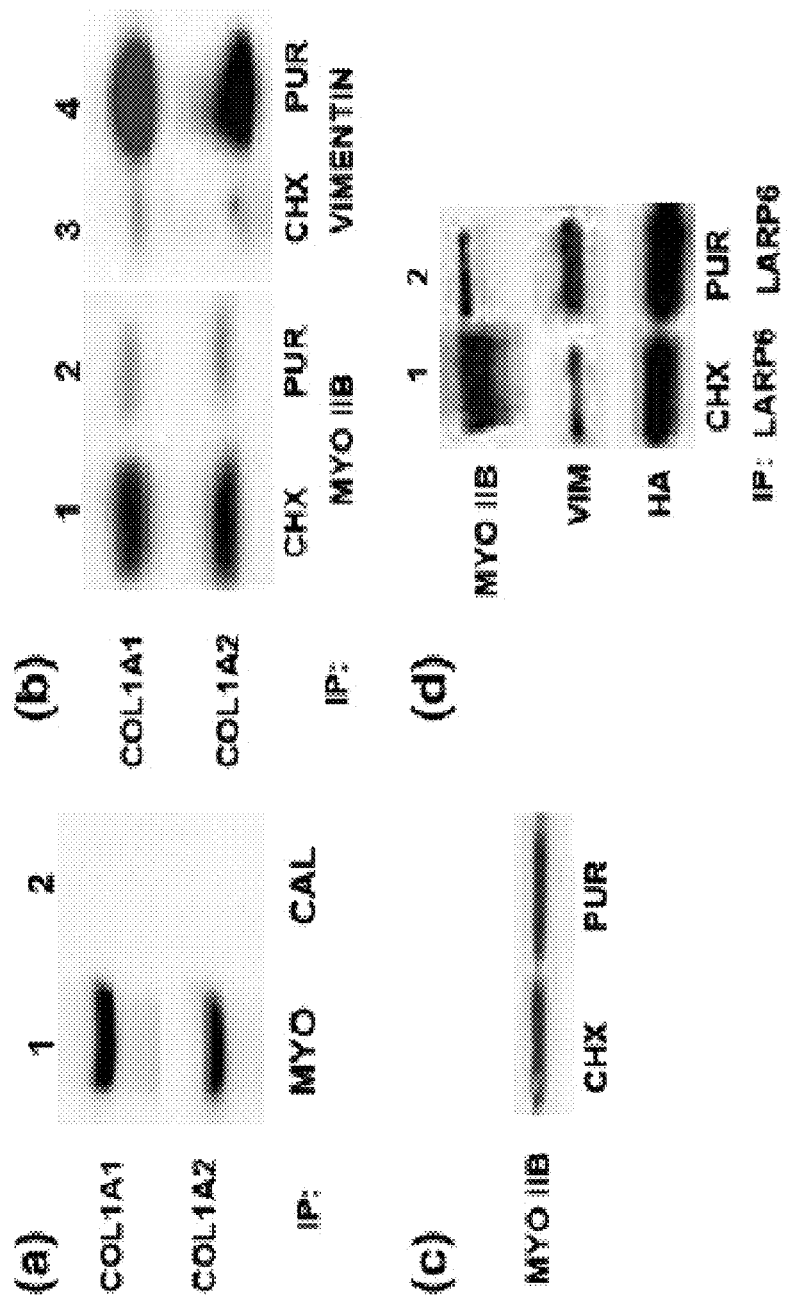
FIG. 9a-d

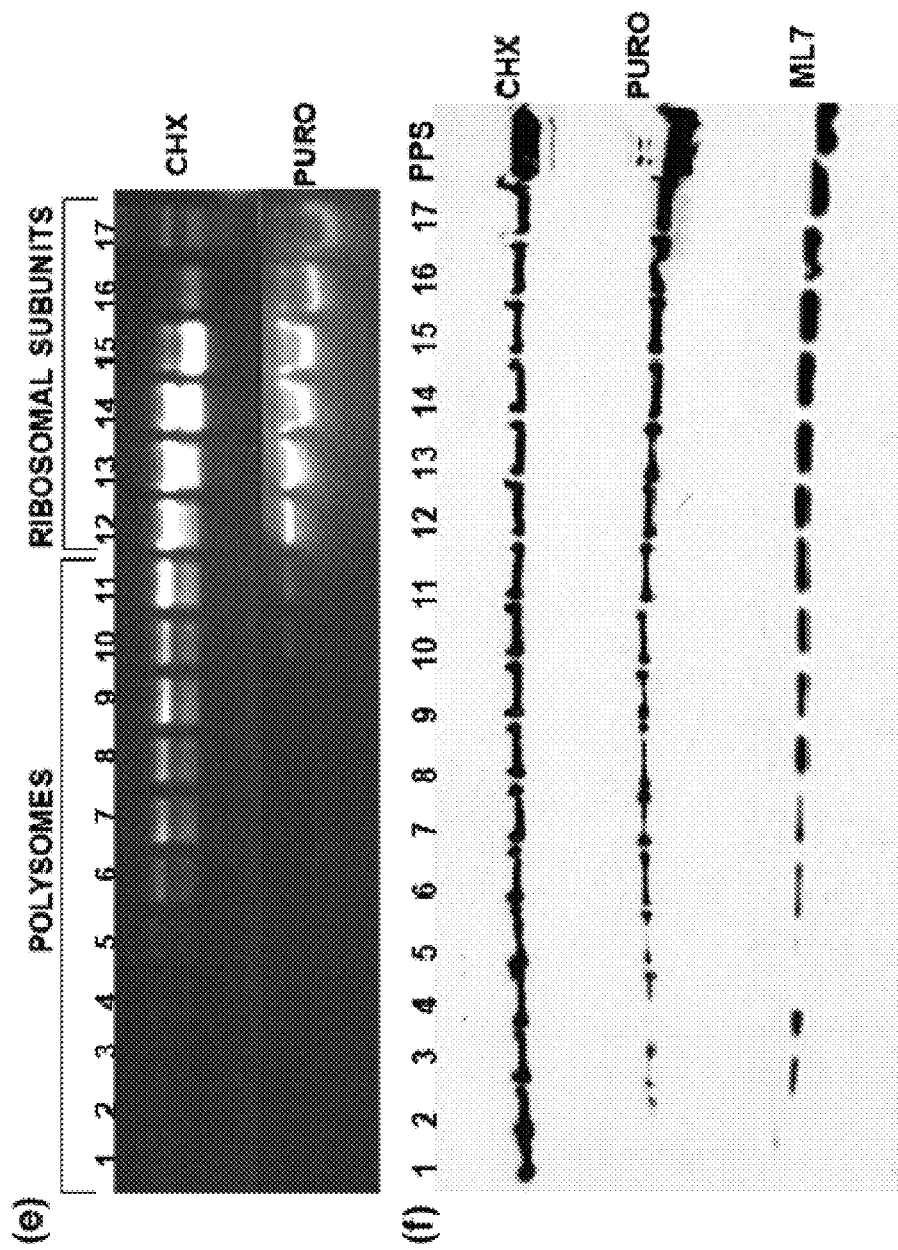
FIG. 9e-f

SEQUENCE LISTING

```
<160> NUMBER OF SEQ ID NOS: 9

<210> SEQ ID NO 1
<211> LENGTH: 491
<212> TYPE: PRT
<213> ORGANISM: Homo sapiens

<400> SEQUENCE: 1

Met Ala Gln Ser Gly Gly Glu Ala Arg Pro Gly Pro Lys Thr Ala Val
 1               5                   10                  15

Gln Ile Arg Val Ala Ile Gln Glu Ala Glu Asp Val Asp Glu Leu Glu
                20                  25                  30

Asp Glu Glu Glu Gly Ala Glu Thr Arg Gly Ala Gly Asp Pro Ala Arg
            35                  40                  45

Tyr Leu Ser Pro Gly Trp Gly Ser Ala Ser Glu Glu Glu Pro Ser Arg
        50                  55                  60

Gly His Ser Gly Thr Thr Ala Ser Gly Gly Glu Asn Glu Arg Glu Asp
    65                  70                  75                  80

Leu Glu Gln Glu Trp Lys Pro Pro Asp Glu Glu Leu Ile Lys Lys Leu
                85                  90                  95

Val Asp Gln Ile Glu Phe Tyr Phe Ser Asp Glu Asn Leu Glu Lys Asp
               100                 105                 110

Ala Phe Leu Leu Lys His Val Arg Arg Asn Lys Leu Gly Tyr Val Ser
           115                 120                 125

Val Lys Leu Leu Thr Ser Phe Lys Lys Val Lys His Leu Thr Arg Asp
       130                 135                 140

Trp Arg Thr Thr Ala His Ala Leu Lys Tyr Ser Val Val Leu Glu Leu
145                 150                 155                 160

Asn Glu Asp His Arg Lys Val Arg Arg Thr Thr Pro Val Pro Leu Phe
                165                 170                 175

Pro Asn Glu Asn Leu Pro Ser Lys Met Leu Leu Val Tyr Asp Leu Tyr
            180                 185                 190

Leu Ser Pro Lys Leu Trp Ala Leu Ala Thr Pro Gln Lys Asn Gly Arg
        195                 200                 205

Val Gln Glu Lys Val Met Glu His Leu Leu Lys Leu Phe Gly Thr Phe
    210                 215                 220
```

```
Gly Val Ile Ser Ser Val Arg Ile Leu Lys Pro Gly Arg Glu Leu Pro
225                 230                 235                 240

Pro Asp Ile Arg Arg Ile Ser Ser Arg Tyr Ser Gln Val Gly Thr Gln
            245                 250                 255

Glu Cys Ala Ile Val Glu Phe Glu Val Glu Ala Ala Ile Lys Ala
        260                 265                 270

His Glu Phe Met Ile Thr Glu Ser Gln Gly Lys Glu Asn Met Lys Ala
    275                 280                 285

Val Leu Ile Gly Met Lys Pro Pro Lys Lys Pro Ala Lys Asp Lys
290                 295                 300

Asn His Asp Glu Glu Pro Thr Ala Ser Ile His Leu Asn Lys Ser Leu
305                 310                 315                 320

Asn Lys Arg Val Glu Glu Leu Gln Tyr Met Gly Asp Glu Ser Ser Ala
            325                 330                 335

Asn Ser Ser Ser Asp Pro Glu Ser Asn Pro Thr Ser Pro Met Ala Gly
            340                 345                 350

Arg Arg His Ala Ala Thr Asn Lys Leu Ser Pro Ser Gly His Gln Asn
        355                 360                 365

Leu Phe Leu Ser Pro Asn Ala Ser Pro Cys Thr Ser Pro Trp Ser Ser
370                 375                 380

Pro Leu Ala Gln Arg Lys Gly Val Ser Arg Lys Ser Pro Leu Ala Glu
385                 390                 395                 400

Glu Gly Arg Leu Asn Cys Ser Thr Ser Pro Glu Ile Phe Arg Lys Cys
            405                 410                 415

Met Asp Tyr Ser Ser Asp Ser Ser Val Thr Pro Ser Gly Ser Pro Trp
            420                 425                 430

Val Arg Arg Arg Gln Ala Glu Met Gly Thr Gln Gly Lys Ser Pro
        435                 440                 445

Gly Thr Ser Pro Leu Leu Ser Arg Lys Met Gln Thr Ala Asp Gly Leu
    450                 455                 460

Pro Val Gly Val Leu Arg Leu Pro Arg Gly Pro Asp Asn Thr Arg Gly
465                 470                 475                 480

Phe His Gly His Glu Arg Ser Arg Ala Cys Val
            485                 490

<210> SEQ ID NO 2
<211> LENGTH: 1476
<212> TYPE: DNA
<213> ORGANISM: Homo sapiens

<400> SEQUENCE: 2
atggcccagt ccggcgggga ggctcggccc gggcccaaga cggcggtgca gatccgcgtc      60
gccatccagg aggccgagga cgtggacgag ttggaggacg aggaggaggg ggcggagact     120
cggggcgccg ggacccggc ccggtacctc agccccggct ggggcagcgc gagcgaggag     180
gagccgagcc gcgggcacag tggcaccact gcaagtggag gtgagaacga gcgtgaggac     240
ctggagcagt agtggaagcc cccggatgag gagttgatca agaaactggt ggatcagatc     300
gaattctact tttctgatga aacctggag aaggacgcct ttttgctaaa acacgtgagg     360
aggaacaagc tgggatatgt gagcgttaag ctactcacat ccttcaaaaa ggtgaaacat     420
cttacacggg actggagaac cacagcacat gctttgaagt attcagtggt ccttgagttg     480
aatgaggacc accggaaggt gaggaggacc accccgtcc cactgttccc caacgagaac     540
ctccccagca agatgctcct ggtctatgat ctctacttgt ctcctaagct gtgggctctg     600
```

-continued

```
gccacccccc agaagaatgg aagggtgcaa gagaaggtga tggaacacct gctcaagctt    660
tttgggactt ttggagtcat ctcatcagtg cggatcctca aacctgggag agagctgccc    720
cctgacatcc ggaggatcag cagccgctac agccaagtgg ggacccagga gtgcgccatc    780
gtggagttcg aggaggtgga agcagccatc aaagcccatg agttcatgat cacagaatct    840
cagggcaaag agaacatgaa agctgtcctg attggtatga agccacccaa aaagaaacct    900
gccaaagaca aaaatcatga cgaggagccc actgcgagca tccacctgaa caagtccctg    960
aacaagagag tcgaggagct tcagtacatg ggtgatgagt cttctgccaa cagctcctct   1020
gaccccgaga gcaaccccac atcccctatg gcgggccgac ggcacgcggc caccaacaag   1080
ctcagcccgt ctggccacca gaatctcttt ctgagtccaa atgcctcccc gtgcacaagt   1140
ccttggagca gccccttggc ccaacgcaaa ggcgtttcca gaaagtcccc actggcggag   1200
gaaggtagac tgaactgcag caccagccct gagatcttcc gcaagtgtat ggattattcc   1260
tctgacagca gcgtcactcc ctctggcagc ccctgggtcc ggaggcgtcg ccaagccgag   1320
atggggaccc aggagaaaag ccccggtacg agtcccctgc tctcccggaa gatgcagact   1380
gcagatgggc tacccgtagg ggtgctgagg ttgcccaggg gtcctgacaa caccagagga   1440
tttcatggcc atgagaggag cagggcctgt gtataa                             1476
```

```
<210> SEQ ID NO 3
<211> LENGTH: 20
<212> TYPE: DNA
<213> ORGANISM: Homo sapiens

<400> SEQUENCE: 3
agaggcgaag gcaacagtcg                                                 20

<210> SEQ ID NO 4
<211> LENGTH: 20
<212> TYPE: DNA
<213> ORGANISM: Homo sapiens

<400> SEQUENCE: 4
gcagggccaa tgtctagtcc                                                 20

<210> SEQ ID NO 5
<211> LENGTH: 20
<212> TYPE: DNA
<213> ORGANISM: Homo sapiens

<400> SEQUENCE: 5
cttcgtgcct agcaacatgc                                                 20

<210> SEQ ID NO 6
<211> LENGTH: 20
<212> TYPE: DNA
<213> ORGANISM: Homo sapiens

<400> SEQUENCE: 6
tcaacaccat ctctgcctcg                                                 20

<210> SEQ ID NO 7
<211> LENGTH: 48
<212> TYPE: RNA
<213> ORGANISM: Mus musculus

<400> SEQUENCE: 7
ccacaaagag ucuacauguc uagggucuag acauguucag cuuugugg                  48
```

```
<210> SEQ ID NO 8
<211> LENGTH: 40
<212> TYPE: RNA
<213> ORGANISM: Mus musculus

<400> SEQUENCE: 8
ggcuuaguau agcgagguuu agcuacacuc gugcugagcc                          40

<210> SEQ ID NO 9
<211> LENGTH: 48
<212> TYPE: RNA
<213> ORGANISM: Mus musculus

<400> SEQUENCE: 9
agaauugcuc guacacagaa uucggucuag agauguucag cuuugugg                 48
```

PROTEIN CONTROLLING SYNTHESIS OF COLLAGEN AND ASSOCIATED METHODS

RELATED APPLICATION

This is a continuation of application Ser. No. 12/898,849 filed Oct. 6, 2010, entitled "Protein Controlling Synthesis of Collagen and Associated Methods," which claims the benefit of provisional application Ser. No. 61/248,928 filed Oct. 6, 2009. Both of these applications are incorporated herein by reference in their entireties.

STATEMENT OF FEDERALLY SPONSORED RESEARCH OR DEVELOPMENT

The invention was made with at least partial support from the U.S. Government. Accordingly, the government may have certain rights in the invention, as specified by law.

SEQUENCE LISTING

This application contains a Sequence Listing electronically submitted via EFS-web to the United States Patent and Trademark Office as a text file named "Sequence_Listing.txt." The electronically filed Sequence Listing serves as both the paper copy required by 37 C.F.R. §1.821(c) and the computer readable file required by 37 C.F.R. §1.821(c). The information contained in the Sequence Listing is incorporated herein by reference in its entirety.

FIELD OF THE INVENTION

The present invention relates to the field of molecular biology and, more particularly, to the biomolecular mechanism controlling synthesis of collagen, which is overproduced in various diseases of fibrosis.

BACKGROUND OF THE INVENTION

Type I collagen is the most abundant protein in the human body. It is composed of two α1(I) polypeptides and one α2(I) polypeptides, which fold into a triple helix.[1] Fibroproliferative disorders are characterized by excessive production of type I collagen by activated fibroblasts and myofibroblasts in tissues that normally do not synthesize type I collagen,[2-5] and they are the major causes of mortality and morbidity, being associated with 45% of deaths in the United States.[6] There is no cure for fibrosis, and excessive collagen production is usually irreversible.[7] All complications of fibroproliferative disorders are due to excessive collagen production, and the molecular mechanism of excessive collagen synthesis must be elucidated to develop antifibrotic drugs. The biosynthesis of type I collagen has multiple steps; however, recently, it became evident that regulation of the stability of collagen mRNAs and their translation constitute the predominant mechanism for high-level synthesis in multiple cell types.[8-12]

In the 5' untranslated region of collagen α1(I), α2(I), and α1(III) mRNAs, there is a conserved 5' stem-loop (5'SL) structure.[13-15] We cloned LARP6, the protein that binds 5'SL with high affinity and specificity.[16] This binding is necessary for high-level expression of type I collagen. We postulated that LARP6 binding serves to prevent premature translation of collagen mRNAs, allowing their subsequent coordinated translation on the membrane of the endoplasmic reticulum (ER).[17] This coordination is evidenced by localization of collagen synthesis into discrete subcellular sites.[16] Translation of collagen α1(I) and α2(I) mRNAs in close proximity to these sites may be needed to increase the local concentration of the polypeptides, which favors the formation of α1(I)/α2(I)/α1(I) heterotrimers. Heterotrimers of type I collagen are almost exclusively synthesized in all tissues,[18] although the homotrimers of α1(I) polypeptides readily form if α2(I) polypeptide is not expressed.[19,20] Folding of collagen triple helix starts with disulfide bonding of two α1(I) polypeptides and one α2(I) polypeptide at the C-terminal end, with subsequent folding into a triple helix. Disulfide-bonded collagen polypeptides were found to be associated with polysomes,[21] suggesting that interchain bonding starts before the release of the polypeptides from the polysomes. Folding and post translational modifications of collagen polypeptides are in kinetic equilibrium, and slow folding results in hypermodification of the polypeptides. Hypermodified collagen peptides fold into an unstable triple helix, resulting in a phenotype of osteogenesis imperfecta.[22,23] Therefore, translational elongation, the rate of modification, and the rate of folding are coordinated. TRAM2 protein, as part of translocons, associates the $Ca^{2+}$ pump Serca2b with the translocons where collagen chains are elongated. It has been proposed that this increases local $Ca^{2+}$ concentration to stimulate collagen-specific molecular chaperones, facilitating folding of the heterotrimer.[12] Despite cloning and characterization of LARP6, the mechanism that coordinates the synthesis of type I collagen is poorly understood. In this work, we describe one key step in the synthesis of type I collagen by profibrotic cells—the interaction of collagen mRNAs with filaments composed of nonmuscle myosin.

SUMMARY OF THE INVENTION

With the foregoing in mind, the present invention advantageously discloses the previously unknown protein with binding affinity for the 5' stem-loop in collagen mRNAs. The present disclosure is the first to identify this protein, LARP6, as responsible for activating translation of collagen mRNAs by linking them with nonmuscle myosin filaments, thus initiating collagen synthesis. Accordingly, interfering with the function of LARP6 should reduce or stop collagen synthesis. The amino acid sequence of the LARP6 polypeptide is shown in the sequence listing as SEQ ID NO:1. The nucleic acid sequence encoding the LARP6 polypeptide is shown in the attached sequence listing as SEQ ID NO:2.

Type I collagen, synthesized in all tissues as the heterotrimer of two α1(I) polypeptides and one α2(I) polypeptide, is the most abundant protein in the human body. Here we have shown that intact nonmuscle myosin filaments are required for the synthesis of heterotrimeric type I collagen. Conserved 5' stem-loop in collagen α1(I) and α2(I) mRNAs binds the RNA-binding protein LARP6. LARP6 interacts with nonmuscle myosin through its C-terminal domain and associates collagen mRNAs with the filaments.

Dissociation of nonmuscle myosin filaments results in secretion of collagen α1(I) homotrimer, diminished intracellular colocalization of collagen α1(I) and α2(I) polypeptides (required for folding of the heterotrimer), and their increased intracellular degradation. Inhibition of the motor function of myosin has similar collagen-specific effects, while disruption of actin filaments has a general effect on protein secretion. Nonmuscle myosin copurifies with polysomes, and there is a subset of polysomes involved in myosin-dependent translation of collagen mRNAs. These results indicate that association of collagen mRNAs with nonmuscle myosin filaments is necessary to coordinately synthesize collagen α1(I) and α2(I) polypeptides. We postulate that LARP6/myosin-dependent mechanism regulates the synthesis of heterotrimeric type I collagen by coordinating the translation of collagen mRNAs.

Those of skill in the art will appreciate that the invention discloses an isolated purified polypeptide having an amino acid sequence consisting essentially of SEQ ID NO:1 and having binding affinity for a 5' stem-loop in collagen mRNAs. Additionally, the invention includes a nucleic acid sequence encoding the polypeptide and consisting essentially of SEQ ID NO:2. Moreover, the polypeptide of the invention displays a further binding affinity for nonmuscle myosin filaments so as to be effective in binding both the nonmuscle myosin filaments and collagen mRNAs.

Yet additionally, the polypeptide disclosed herein may be employed in a method of screening an agent for ability to interfere with collagen synthesis. The method comprises reacting the disclosed polypeptide with collagen mRNAs in presence of the agent, and detecting if the agent has interfered with binding of the polypeptide to the mRNAs.

An alternate embodiment of the method includes reacting the disclosed polypeptide with nonmuscle myosin filaments in presence of an agent, and determining if the agent has interfered with binding of the polypeptide to the nonmuscle myosin filaments.

Yet another embodiment of the method of the invention calls for the employing the disclosed polypeptide in a method of testing an agent for ability to interfere in collagen synthesis. This embodiment of the method comprises reacting the disclosed polypeptide with collagen mRNAs and with nonmuscle myosin filaments in presence of the agent, and detecting if the agent has interfered with binding of the polypeptide to either of both the mRNAs or the nonmuscle myosin filaments.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some of the features, advantages, and benefits of the present invention having been stated, others will become apparent as the description proceeds when taken in conjunction with the accompanying drawings, presented for solely for exemplary purposes and not with intent to limit the invention thereto, and in which the following descriptions of the figures apply.

FIG. 9 Association of nonmuscle myosin with polysomes. (a) Specific immunoprecipitation of collagen mRNAs with nonmuscle myosin. Immunoprecipitation with anti-myosin IIB antibody (MYO; lane 1) and anti-calnexin antibody (CAL; lane 2), and analysis of immunoprecipitate by RT-PCR with primers specific for collagen α1(I) (COL1A1) and collagen α2(I) (COL2A2). (b) Distribution of collagen mRNAs between nonmuscle myosin and vimentin. Immunoprecipitation with anti-myosin IIB antibody (lanes 1 and 2) and anti-vimentin antibody (lanes 3 and 4) from lung fibroblasts treated with cycloheximide (CHX) or puromycin (PUR). Immunoprecipitate was analyzed by RT-PCR with primers specific for collagen α1(I) (COL1A1) and collagen α2(I) (COL2A2). (c) Levels of nonmuscle myosin IIB in cycloheximide-treated and puromycin-treated cells are similar. Western blot analysis of nonmuscle myosin IIB (MYO IIB) in cells treated with cycloheximide (CHX) and puromycin (PUR). (d) Distribution of LARP6 between nonmuscle myosin and vimentin. Immunoprecipitation of HA-tagged LARP6 from lung fibroblasts treated with cycloheximide (CHX) and puromycin (PUR). Immunoprecipitate was analyzed by Western blot analysis using antibodies against nonmuscle myosin IIB (MYO IIB), vimentin (VIM), and HA-tag (HA) as control for immunoprecipitation efficiency. (e) Identification of puromycinsensitive polysomes. Polysomes from lung fibroblasts treated with cycloheximide (CHX) and puromycin (PUR) were fractionated on a 15-45% continuous sucrose gradient, and fractions were analyzed for the presence of ribosomal RNA. Fraction 1, 45% sucrose; fraction 17, 15% sucrose. (f) Nonmuscle myosin copurifies with polysomes. Polysomes were fractionated as in (d), and the fractions were probed for the presence of nonmuscle myosin using Western blot analysis. PPS, postpolysomal supernatant. Bottom: The cells were treated with ML-7 prior to fractionation of polysomes.

DETAILED DESCRIPTION OF THE PREFERRED EMBODIMENT

Figure 1A:
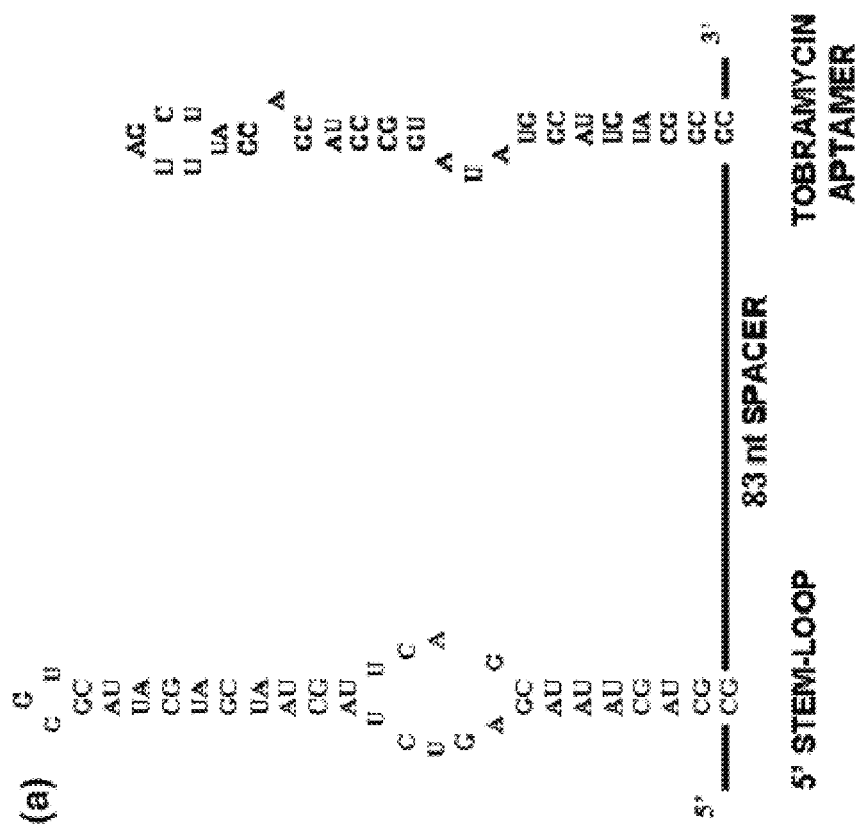
FIG. 1 shows tobramycin affinity purification of 5'SL-associated proteins: (a) mouse collagen mRNA 5'SL, wild type (SEQ ID NO:7) and 5'SL/tobramycin aptamer bait (SEQ ID NO:8); (b) proteins specifically pulled down with 5'SL bait; Coomassie-stained SDS-PAGE gel of proteins pulled down with 5'SL bait (lane 2) or inverted 5'SL bait (CON; lane 1); lane 3, size marker; nonmuscle myosin IIB (MYO IIB) and vimentin (VIM) are indicated by arrows.

The present invention will now be described more fully hereinafter with reference to the accompanying drawings, in which preferred embodiments of the invention are shown.

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention.

Moreover, it should also be understood that any temperature, weight, volume, time interval, pH, salinity, molarity or molality, range, concentration and any other measurements, quantities or numerical expressions given herein are intended to be approximate and not exact or critical figures unless expressly stated to the contrary. Accordingly, where appropriate to the invention and as understood by those of skill in the art, it is proper to describe the various aspects of the invention using approximate or relative terms and terms of degree commonly employed in patent applications, such as: so dimensioned, about, approximately, substantially, essentially, consisting essentially of, comprising, and effective amount.

Further, any publications, patent applications, patents, and other references mentioned herein are incorporated by reference in their entirety as if they were part of this specification. However, in case of conflict, the present specification, including any definitions, will control. In addition, the materials, methods and examples given are illustrative in nature only and not intended to be limiting.

Accordingly, this invention may be embodied in many different forms and should not be construed as limited to the illustrated embodiments set forth herein. Rather, these illustrated embodiments are provided so that this disclosure will be thorough, complete, and will fully convey the scope of the invention to those skilled in the art. Other features and advantages of the invention will be apparent from the following detailed description, and from the claims.

Materials and Methods

Chemicals and Cells

ML-7, blebbistatin, cytochalasin B, puromycin, and cycloheximide were purchased from Sigma. ML-7 was used at 40 µM, blebbistatin was used at 100 µM, and cytochalasin B was used at 20 µM. Cells were incubated with the drugs for 16 h before analysis. Puromycin (200 µg/ml) and cycloheximide (100 µg/ml) were added to the cells for 2 h. Human lung fibroblasts have been described previously.16 Scleroderma fibroblasts were purchased from the European Collection of Cell Cultures (cell line BM0070) and derived from the skin of a scleroderma patient. MEFs were derived from knock-in mice in which the 5'SL of the collagen α1(I) gene has been mutated (Parsons et al., submitted). Several independent cell isolates were used throughout the study. All cells were cultured in Dulbecco's modified Eagle's medium supplemented with 10% fetal bovine serum for up to 10 passages. Plasmid constructs and adenovirus preparation. The HA-tagged LARP6 clone and the deletion mutants have been described previously.[16] Adenoviruses were constructed by recloning of the constructs into the pAdCMVTRACK vector, followed by recombination with the pAdEasy vector and amplification, as described previously.[48] Expression of each construct was verified by Western blot analysis. The viruses made express both the full-size test protein and the green fluorescent protein (GFP), which is encoded by an independent transcription unit.[48] Expression of GFP served as control for viral transduction. RT-PCR analysis Total cellular RNA was isolated using an RNA isolation kit (Sigma). RT-PCRs were performed with 100 ng of total RNA or using rTth reverse transcriptase (Boca Scientific, Boca Raton, Fla.). [$^{32}$P]dCTP was included in the PCR step to label the products, which were resolved on sequencing gels, as described previously.[8,31,49,50] When RNA from polysomal fractions was analyzed, an equal aliquot of each fraction was used. The number of cycles was adjusted to within the linear range of the reaction. The primers used for RT-PCR were as follows: h-collagen α1(I), 5' primer AGAGGCGAAGGCAACAGTCG (SEQ ID NO:3) and 3' primer GCAGGGCCAATGTCTAGTCC (SEQ ID NO:4); h-collagen α2(I), 5' primer CTTCGTGCCTAGCAACATGC (SEQ ID NO:5) and 3' primer TCAACACCATCTCTGC-CTCG (SEQ ID NO:6).

Antibodies

Anti-HA antibody and anti-GFP antibody were obtained from Sigma; anti-MYH10 antibody was obtained from the University of Iowa hybridoma bank; antinucleolin antibody and anti-vimentin antibody were obtained from Santa Cruz Biotechnology; anti-collagen α1(I) antibody was obtained from Rockland; anti-collagen α2(I) antibody was obtained from Cell Signaling; antifibronectin antibody and anti-tubulin antibody were obtained from BD Biosciences; and anti-LARP6 antibody was obtained from Abnova.

Western Blot Analysis and Immunostaining

Protein concentration was estimated by the Bradford assay, with bovine serum albumin as standard.[51] Western blot analyses of cellular proteins were performed using 50 µg of protein. For Western blot analysis of secreted proteins, equal numbers of cells were seeded, serum-free medium was added to the cells, and incubation continued for 3 h. The medium was collected, and an aliquot was analyzed directly by Western blot analysis. Use of serum free medium in collecting secreted proteins is essential because fetal calf serum contains substantial amounts of collagen and fibronectin.[15,31] For immunostaining, cells were seeded onto glass coverslips. After treatment, the cells were fixed with 4% paraformaldehyde for 30 min at room temperature and permeabilized with 0.5% Triton X-100 in phosphatebuffered saline (PBS) for 10 min. After the cells had been blocked with 10% goat serum/5% bovine serum albumin in PBS for 1 h at room temperature, they were incubated with primary antibody overnight at 4° C., washed, and visualized with AlexaFluor594-conjugated or Cy-2-conjugated secondary antibodies. The cells were mounted using VECTASHIELD mounting medium containing 4° C., 6-diamidino-2-phenylindole (Vector Laboratories), and images were taken by a Leica TCS SP2 AOBS laser confocal microscope equipped with a Chameleon Ti: Sapphire multiphoton laser. Optical sections were processed with LCSLite software.

Immunoprecipitation

Cell extracts were prepared in lysis buffer [10 mM Kcl, 1.5 mM MgCl2, 10 mM Tris.HCl (pH 7.5), 0.5% NP-40, and 170 µg/ml phenylmethylsulfonyl fluoride]. After removal of nuclei by centrifugation, the clear lysate was incubated with 1 µg of antibody for 1 h at 4° C. Twenty microliters of washed protein A/G plus agarose (Santa Cruz Biotechnology) was added, and incubation continued for an additional 3 h. After the beads had been washed three times in PBS, immunoprecipitated complexes were dissolved in SDS-PAGE loading dye or RNA was extracted. In reactions in which RNase A was added after immunoprecipitation, 0.2 µg/µl RNase A was incubated with A/G plus agarose beads for 15 min at room temperature and then washed two times in PBS.

Tobramycin Affinity Pull-Downs

Tobramycin affinity pull-downs were performed as described previously.[25] A chimeric RNA bait was made by in vitro transcription from a template with collagen α1(I) 5' SL, followed by tobramycin aptamer. The control bait had inverted 5'SL and tobramycin aptamer. Cytosolic extracts were prepared from human lung fibroblasts, and the baits were incubated in the extract for 30 min on ice. Tobramycin was coupled to agarose beads as described previously,[25] and tobramycin beads were added to the extract. After 30 min of incubation, the beads were pelleted and washed five times, and the bound proteins were eluted by 5 mM free tobramycin. The purified proteins were resolved on SDS-PAGE gel and visualized by Coomassie staining. The proteins specifically purified by the 5'SL bait were excised and in-gel digested with trypsin. Eluted peptides were sequenced by LC-coupled ESI-MS/MS on an LTQ XL instrument (Thermo Scientific). The corresponding proteins were identified by searching against all entries in the National Center for Biotechnology Information nonredundant database using the search engine MASCOT (Matrix Science).

Fractionation of Polysomes

Polysomes were fractionated as described previously.[16] Sucrose fractions (0.5 ml) were collected, and total RNA was extracted by phenol/chloroform and isopropanol precipitation. Equivalent amounts of each fraction were analyzed by RT-PCR. Total proteins were extracted from sucrose fractions by trichloroacetic acid precipitation, and equivalent amounts were analyzed by Western blot analysis.

Results

Nonmuscle Myosin Copurifies with 5'SL RNA

Figure 1B:
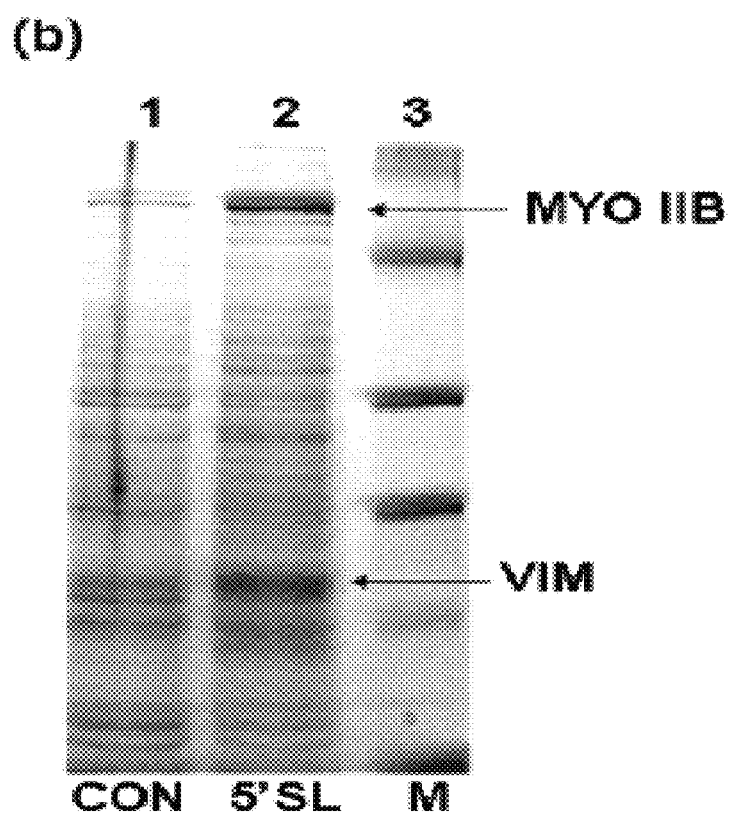

LARP6 had been cloned before as a protein that directly binds 5'SL of collagen mRNAs;[16] however, other proteins that associate in complex with LARP6 and 5'SL have been unknown. To identify these proteins, we performed tobramycin affinity purification by attaching a tobramycin aptamer to the 5'SL RNA (FIG. 1a). Affinity purification using a tobramycin aptamer has been described for purification of splicing complexes.[24,25] After incubation of the collagen 5'SL/tobramycin aptamer RNA in cytosolic extracts of human lung fibroblasts, the bound proteins were pulled down with tobramycin agarose and eluted with an excess of free tobramycin (FIG. 1b, lane 2). Inverted 5'SL fused to the aptamer was used as control (lane 1). The two most prominent proteins specifically pulled down with 5'SL were identified as nonmuscle myosin IIB and vimentin (FIG. 1b, arrows). LARP6 was found as a minor band in these experiments. Identification of nonmuscle myosin IIB as the protein that copurifies with collagen 5'SL was unexpected, as there have been no reports on the role of nonmuscle myosin in the synthesis of type I collagen.

Interaction of Collagen mRNAs with Nonmuscle Myosin

Since LARP6 is the only protein that directly binds 5'SL,[16] it is likely that nonmuscle myosin had been tethered to 5'SL by protein interaction with LARP6. To verify if LARP6 and nonmuscle myosin interact, we performed coimmunoprecipitation experiments. LARP6 has four domains: the N-terminal domain of unknown function, the La homology domain found in other LARPs,[26] the unique RNA binding domain necessary for binding 5'SL,[16] and the C-terminal domain of unknown function (FIG. 2a). To identify which domain is needed for the interaction with myosin IIB, we expressed HAtagged full-size LARP6 and HA-tagged LARP6 lacking the C-terminal domain (ΔC-LARP6) and performed immunoprecipitations with anti-HA antibody. While myosin IIB coimmunoprecipitated with the full-size LARP6 (FIG. 2b, lane 1), it failed to coimmunoprecipitate with ΔC-LARP6 (lane 2) or with the control RNA-binding protein RBMS327 (lane 3). Myosin IIA was also coimmunoprecipitated with full-size LARP6, but not with ΔC-LARP6 (FIG. 2c), suggesting that LARP6 interacts with both major isoforms of nonmuscle myosin through its C-terminal domain. The C-terminal domain of LARP6 is not needed for binding 5'SL.[16] We also assessed if the interaction between LARP6 and nonmuscle myosin is dependent on intact RNA by digesting the samples with RNase A prior to analysis (FIG. 2d). Immunoprecipitation of LARP6 pulled down myosin IIB regardless of RNase A digestion (lanes 1 and 2), suggesting that these proteins form a complex by protein interactions. These interactions were specific because fibronectin and RBMS3 were not coimmunoprecipitated (lane 3). Collagen α1(I) and α2(I) mRNAs were also found to be immunoprecipitated with nonmuscle myosin in an 5'SL-dependent manner (described in FIG. 8).

Figure 3:
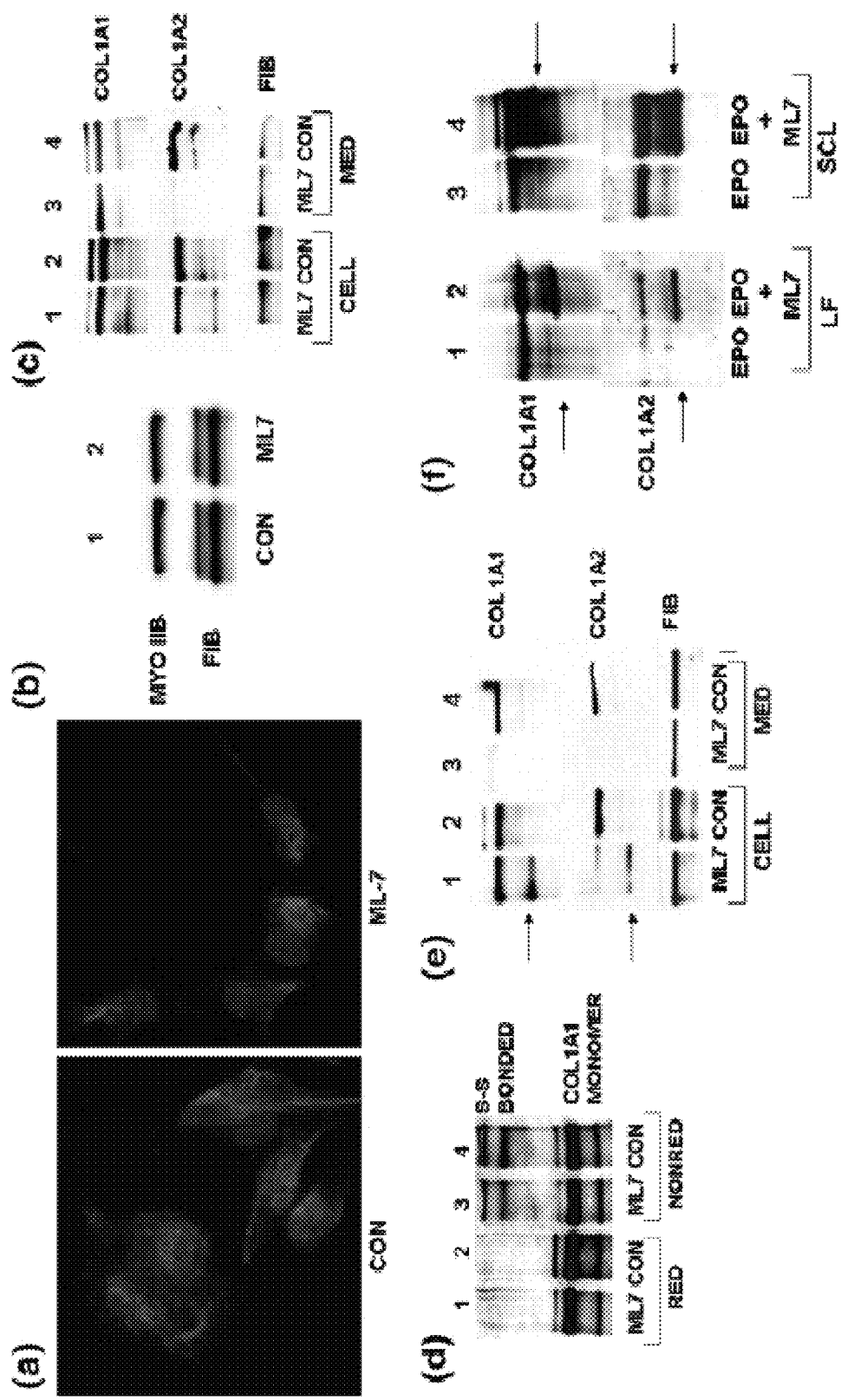
FIG. 3 Disruption of nonmuscle myosin by ML-7 results in secretion of homotrimeric type I collagen. (a) ML-7 disrupts nonmuscle myosin filaments. Immunostaining of nonmuscle myosin IIB in control lung fibroblasts (CON) and in lung fibroblasts treated with ML-7 (ML-7). (b) ML-7 does not change the total level of nonmuscle myosin protein. Western blot analysis of control cells (lane 1) and cells treated with ML-7 (lane 2) using anti-myosin IIB antibody (MYO IIB). Fibronectin (FIB), loading control. (c) Effect of ML-7 on collagen secretion from lung fibroblasts. Western blot analysis of cellular proteins from control cells (lane 2) and ML-7-treated cells (lane 1), and of medium proteins from control cells (lane 4) and ML-7-treated cells (lane 3). COL1A1, collagen α1(I) polypeptide; COL1A2, collagen α2(I) polypeptide; FIB, fibronectin as loading control. (d) Homotrimeric triple helix in the medium of ML-7-treated cells. The medium samples from (c) were analyzed under reducing conditions (lanes 1 and 2) and nonreducing conditions (lanes 2 and 3) with antibody specific for collagen α1(I) polypeptide. Migration of collagen α1(I) monomers (COL1A1) and disulfide-bonded chains (S—S BONDED) is indicated. (e) Effect of ML-7 on collagen secretion from scleroderma fibroblasts. Experiment as in (c), but primary scleroderma skin fibroblasts were used. Putative cellular degradation products of collagen α1(I) and α2(I) polypeptides are indicated by arrows. (f) Increased intracellular degradation of collagen polypeptides in ML-7-treated cells. Lung fibroblasts (lanes 1 and 2) and scleroderma fibroblasts (lanes 3 and 4) were treated with epoxomycin alone (lanes 1 and 3) and with epoxomycin and ML-7 (lanes 2 and 4). Intracellular collagen was analyzed by Western blot analysis using antibodies against collagen α1(I) polypeptide (COL1A1) and α2(I) polypeptide (COL1A2). Putative degradation products are indicated by arrows.
Figure 4:
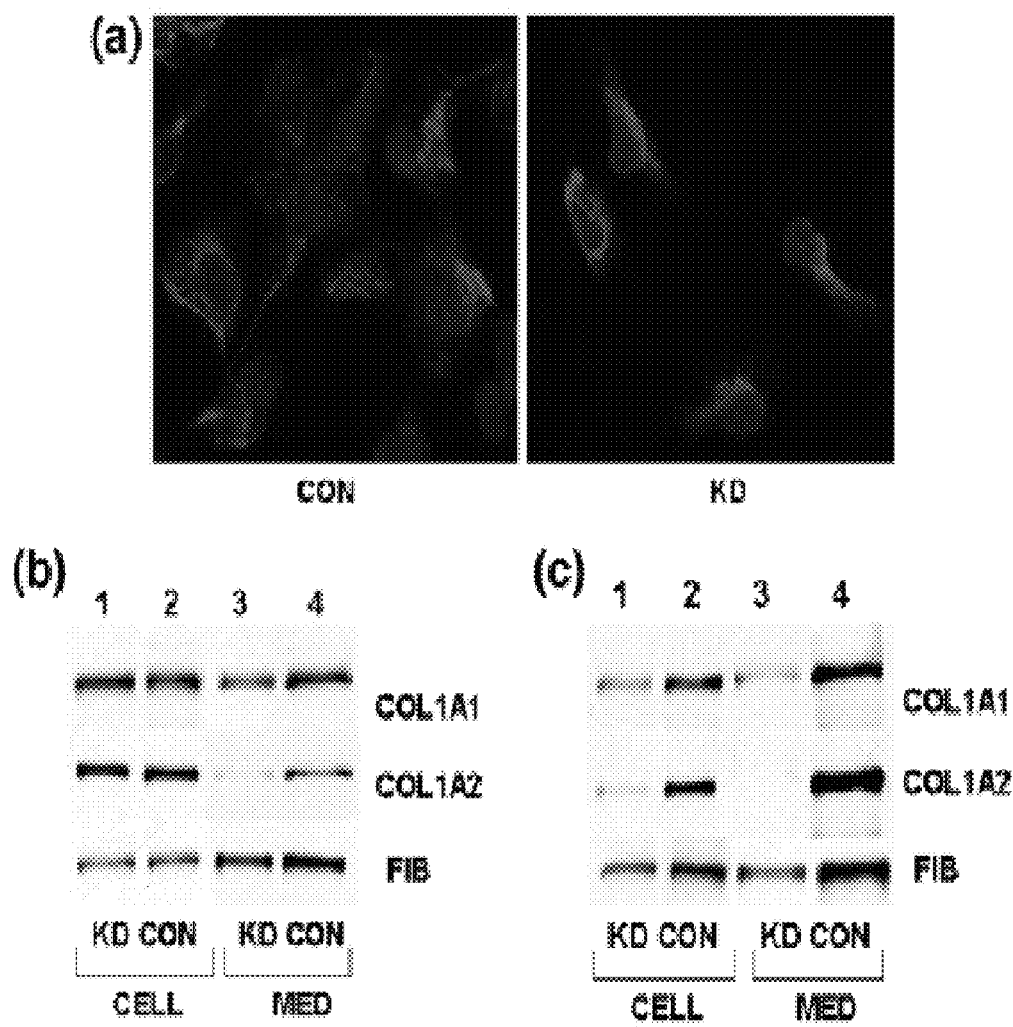
FIG. 4. Disruption of nonmuscle myosin filaments by a dominant negative isoform of MLCK results in secretion of homotrimeric type I collagen. (a) Disruption of nonmuscle myosin filaments by overexpression of a kinase-dead isoform of MLCK. Immunostaining of myosin IIB in lung fibroblasts infected with control adenovirus (CON) and with adenovirus expressing a kinase-dead isoform of MLCK (KD). (b) Diminished secretion of collagen α2(I) polypeptide from lung fibroblasts overexpressing KD-MLCK. Cellular level (lanes 1 and 2) and medium level (lanes 3 and 4) of collagen α1(I) polypeptide (COL1A1) and α2(I) polypeptide (COL1A2) analyzed for cells transduced with control adenovirus (CON; lanes 2 and 4) and adenovirus expressing a kinase-dead isoform of MLCK (KD; lanes 1 and 3). Fibronectin is shown as loading control. (c) Same experiment as in (b), but using scleroderma fibroblasts.

Integrity of Nonmuscle Myosin Filaments is Necessary for Secretion of Type I Collagen To assess the role of nonmuscle myosin in collagen synthesis, we disrupted nonmuscle myosin filaments in two different cell types: primary human lung fibroblasts and primary scleroderma skin fibroblasts. These cells are responsible for lung and skin fibrosis. Nonmuscle myosin filaments were disrupted either by treatment of the cells with ML-7[28] or by overexpression of a kinase-dead myosin light-chain kinase (KD-MLCK) mutant (a kind gift of Dr. P. Gallagher, Indiana University).[29,30] ML-7 is a specific inhibitor of myosin light-chain kinase (MLCK),[28] and inhibition of MLCK leads to disassembly of myosin IIA and IIB filaments.[29,30] FIG. 3a shows immunostaining of human lung fibroblasts for myosin IIB without ML-7 treatment (left) and with ML-7 treatment (right). In untreated cells, myosin filaments are prominent, while in ML-7-treated cells, myosin staining is confined around the nucleus. The same effect was seen in scleroderma fibroblasts. The total level of myosin IIB remained unchanged on Western blot analysis (FIG. 3b). The levels of collagen α1(I) and α2(I) mRNAs were also not significantly affected by ML-7 (see FIG. 8). To assess the effect of ML-7 on collagen protein synthesis and secretion, we analyzed the levels of collagen α1(I) and α2(I) polypeptides in the intracellularly space and in the medium using Western blot analysis and chain-specific antibodies.[12,15,31-33] ML-7 treatment profoundly affected the secretion of type I collagen, but the effect differed in the two types of primary fibroblasts. In lung fibroblasts, the intracellular level of collagen a1 and a2 polypeptides was not significantly affected by ML-7 treatment (FIG. 3c, lanes 1 and 2). In the medium, collagen α1(I) polypeptide was found in similar amounts in control and ML-7-treated cells; however, collagen α2(I) polypeptide was secreted only in trace amounts after ML-7 treatment (lanes 3 and 4). The absence of α2(I) polypeptide in the medium suggests that ML-7 uncoupled the secretion of α1(I) and α2(I) chains. α2(I) polypeptide cannot be efficiently secreted without folding with α1(I) polypeptide.34 The secretion of fibronectin was not affected, suggesting that the general machinery for protein secretion was intact. Immunostaining for the ER marker protein calnexin did not show a difference between ML-7-treated cells and control cells, suggesting that organization of the ER was also not significantly changed. To assess if the secreted α1(I) polypeptides had been secreted as disulfide-bonded homotrimers, we performed Western blot analysis under nonreducing conditions (FIG. 3d). In ML-7-treated cells, a similar fraction of disulfide-bonded collagen was found as in control cells (compare lanes 3 and 4). However, since α2(I) polypeptide was absent in the cell medium of ML-7-treated cells, the bands must represent disulfide-bonded collagen α1(I) chains. The α2(I) antibody could not recognize the polypeptide under nonreducing conditions, so we could not directly test its presence in S—S bonded collagen. Since there are reports that ML-7 can cause apoptosis of epithelial cells, we tested if ML-7 caused apoptosis of the primary fibroblasts. Treatment with ML-7 increased the percentage of apoptotic cells in lung fibroblasts from 2.2% to 4.2% and did not have an effect on the percentage of apoptotic scleroderma fibroblasts (0.3%). Therefore, we concluded that increased apoptosis is not responsible for the observed effects of ML-7. In scleroderma skin fibroblasts, the intracellular level of collagen α1(I) polypeptide was not changed with ML-7 treatment; however, the level of α2(I) polypeptide was reduced (FIG. 3e, lanes 1 and 2). In multiple experiments, but only in ML-7-treated samples, we have noticed the appearance of bands indicated by arrows in FIG. 3e. They likely represent degradation products of α1(I) and α2(I) polypeptides (see the text below). In the medium, collagen α1(I) polypeptide was barely detectable, while collagen α2(I) polypeptide was absent (lanes 3 and 4). Thus, in scleroderma fibroblasts, ML-7 treatment almost completely abolished collagen secretion. The secretion of fibronectin was not affected. Although collagen α2(I) polypeptide was not secreted into the medium of lung fibroblasts and both collagen polypeptides were not secreted from scleroderma fibroblasts, their intracellular levels were not increased after ML-7 treatment. To test if they have been subjected to accelerated degradation, we treated the cells with the proteosome inhibitor epoxymycin in combination with ML-7. The intra intracellular level of both collagen polypeptides significantly increased with the combined treatment compared to treatment with epoxymycin alone (FIG. 30. An additional product of approximately 120 kDa (FIG. 3f, arrow) was prominently seen in the samples treated with epoxomycin and ML-7 (lanes 2 and 4), but not in the samples treated with epoxomycin alone (lanes 1 and 2). This is the same degradation product seen in scleroderma fibroblasts without epoxomycin (FIG. 3e), but which accumulated to a high level when proteosomal degradation was inhibited. We concluded from these experiments that the failure of lung fibroblasts to secrete collagen α2(I) polypeptide and the failure of scleroderma fibroblasts to secrete both polypeptides after ML-7 treatment are due to their inefficient folding into a heterotrimer and their accelerated intracellular degradation. To exclude that nonspecific effects of ML-7 are responsible for the perturbation in collagen synthesis, we repeated the analysis after overexpressing KD-MLCK. This isoform acts as a dominantnegative protein for myosin filaments assembly. CK isoform was constructed as adenovirus for efficient delivery into the primary fibroblasts. Overexpression of KD-MLCK resulted in disassembly of the filaments in lung fibroblasts (FIG. 4a, right), similar to that seen upon ML-7 treatment. The same effect was seen in scleroderma fibroblasts. In lung fibroblasts, KD-MLCK dramatically reduced the secretion of α2(I) polypeptide, with little effect on the secretion of α1(I) polypeptide (FIG. 4b, lane 3). In scleroderma fibroblasts, it reduced the level of both polypeptides intracellularly (FIG. 4c, lane 1); however, this time, we did not observe the characteristic degradation products seen after ML-7 treatment. In the medium, α1(I) polypeptide was dramatically reduced, while α2(I) polypeptide was absent (lane 3). Thus, a similar effect on collagen synthesis was seen when nonmuscle myosin filaments were disrupted by KD-MLCK.

Figure 5B:
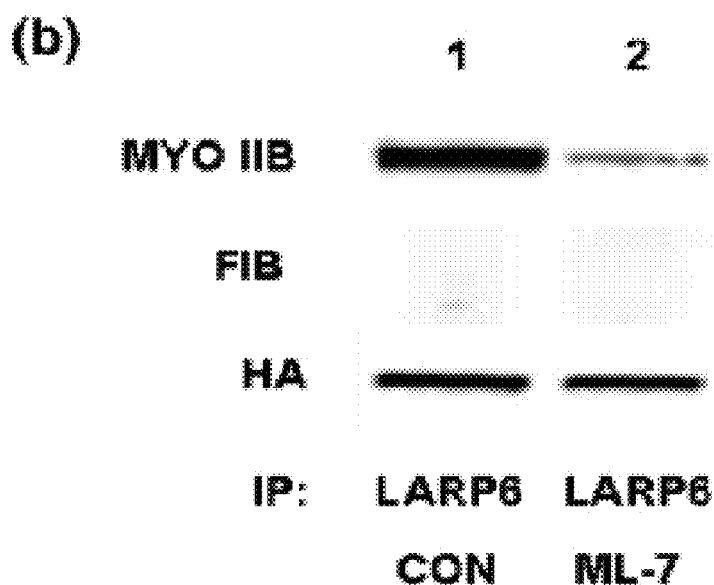
FIG. 5 Colocalization of collagen α1(I) and α2(I) polypeptides in the cell. (a) Collagen α1(I) and α2(I) polypeptides do not colocalize after ML-7 treatment. Immunostaining with collagen α1(I)-specific antibody (COL1A1; green) and collagen α2(I) antibody (COL1A2; red), and the overlaid image (MERGE) in control cells (CON; top) and ML-7-treated cells (ML-7; bottom). (b) Coimmunoprecipitation of nonmuscle myosin with LARP6 is decreased after ML-7 treatment. Immunoprecipitation of HA-tagged LARP6 from control lung fibroblasts (lane 1) and from lung fibroblasts treated with ML-7 (lane 2), analyzed by Western blot analysis using anti-myosin IIB antibodies (MYO IIB), anti-fibronectin antibody, and anti-HA antibody (as control for precipitation efficiency).

To fold into a collagen heterotrimer, the α1(I) and α2(I) polypeptides must colocalize in the lumen of the ER. Since ML-7 treatment of lung fibroblasts did not affect the cellular level of the individual collagen polypeptides (FIG. 3b), we used this cell type to assess if their subcellular colocalization was affected by ML-7. Using chain-specific antibodies for immunostaining, we observed a high degree of colocalization of α1(I) and α2(I) polypeptides in control cells (FIG. 5a, top). This colocalization was confined to the ER upon costaining with the ER marker calnexin. However, in ML-7-treated cells, a significant fraction of α2(I) polypeptide (red) was not colocalized with α1(I) polypeptide (green) (FIG. 5a, bottom). This is consistent with lack of their folding into the heterotrimer. The interaction between LARP6 and nonmuscle myosin was also diminished by disruption of the filaments (FIG. 5b). ML-7 did not change the level of myosin IIB protein, only its polymerization (FIG. 3a); however, significantly less myosin IIB was pulled down with LARP6 from ML-7-treated cells (lane 2) than from control cells (lane 1). From these experiments, we concluded that tethering of collagen mRNAs to nonmuscle myosin filaments by LARP6 coordinates the synthesis of α1(I) and α2(I) polypeptides for productive secretion of the heterotrimeric type I collagen.

Figure 6:
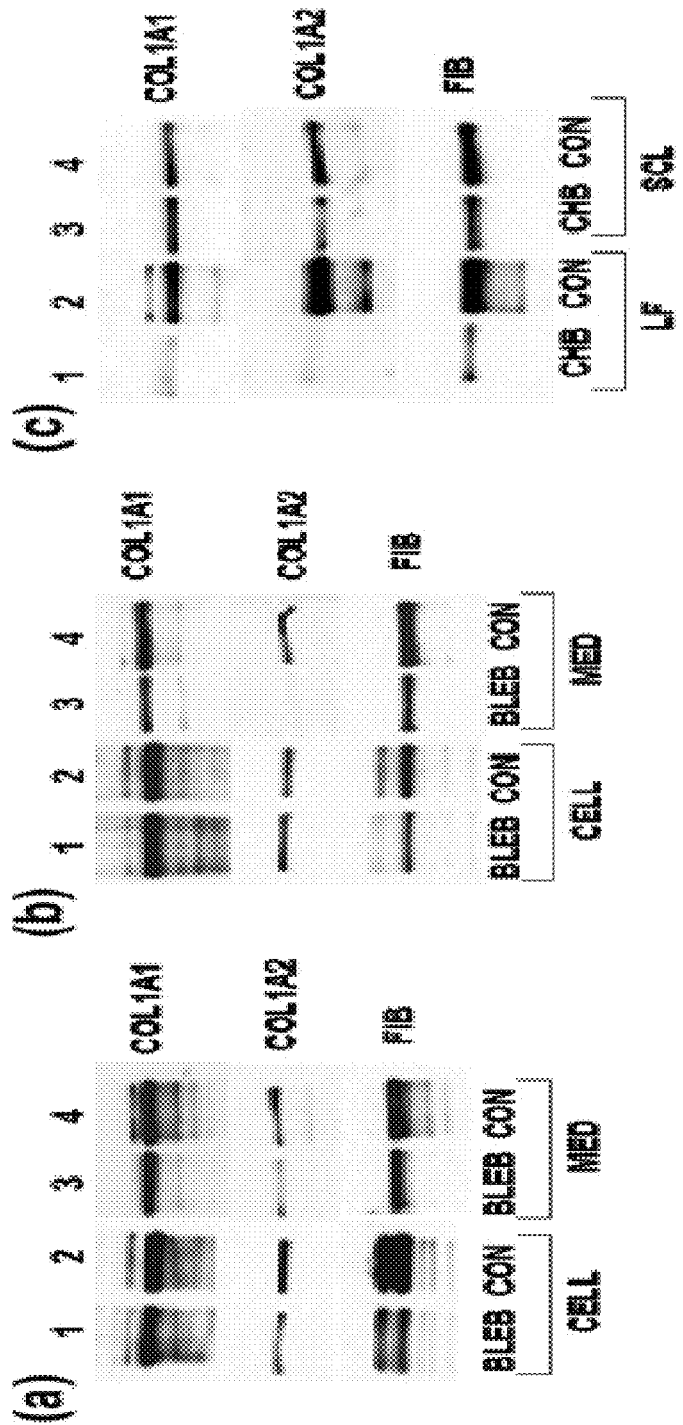
FIG. 6. Motor function of nonmuscle myosin is required for secretion of type I collagen. (a) Effect of blebbistatin on collagen secretion from lung fibroblasts. Western blot analysis of cellular proteins from control cells (lane 2) and blebbistatin-treated cells (lane 1), and of medium proteins from control cells (lane 4) and blebbistatin-treated cells (lane 3). COL1A1, collagen α1(I) polypeptide; COL1A2, collagen α2(I) polypeptide; FIB, fibronectin as loading control. (b) Effect of blebbistatin on collagen secretion from scleroderma fibroblasts. Experiment as in (a), except that primary scleroderma skin fibroblasts were used. (c) Effect of actin filament disruption. Western blot analysis of medium proteins from lung fibroblasts (LF; lanes 1 and 2), scleroderma fibroblasts (SCL; lanes 3 and 4), control cells (CON; lanes 2 and 4), and cells treated with cytochalasin B (CHB; lanes 1 and 3). Western blot analysis was probed with antibodies against collagen α1(I) polypeptide (COL1A1), collagen α2(I) polypeptide (COL1A2), and fibronectin (FIB) as loading control.

Blebbistatin is an inhibitor of the ATPase function of nonmuscle myosin and blocks the motor function of filaments. To assess if the myosin motor is required for collagen synthesis, we treated the cells with blebbistatin and analyzed collagen α1(I) and α2(I) polypeptides. Blebbistatin reduced the secretion f α2(I) polypeptide from lung fibroblasts (FIG. 6a, lane 3) and abolished its secretion from scleroderma fibroblasts (FIG. 6b, lane 3), while minimally affecting the secretion of α1(I) polypep-tide in both cell types. The cellular levels of both collagen polypeptides were unchanged. There was a small effect on the expression of fibronectin, which was reduced intracellularly and in the medium. Therefore, we included another loading control for cellular fractions (tubulin), which showed equal loading. We concluded that the motor function of myosin is involved in coordinating the secretion of type I collagen. It is possible that the effect of myosin disruption is indirect due to the lack of motility of actin filaments. Therefore, we disrupted actin filaments with cytochalasin B38 and repeated the experiments (FIG. 6c). In lung fibroblasts, cytochalasin B diminished the secretion of collagen α1(I) and α2(I) polypeptides, but also had an effect on fibronectin secretion (lane 1). This suggests that the general secretion machinery may have been affected. In scleroderma fibroblasts, there was no effect on the secretion of collagen α1(I) polypeptide and a small effect on the secretion of α2(I) polypeptide and fibronectin. Thus, the effects of nonmuscle myosin disruption are specific for collagen, while actin disruption has effects on the general protein secretion machinery.

The Effect of Nonmuscle Myosin on Collagen Synthesis is Mediated by 5'SL

Figure 7A:
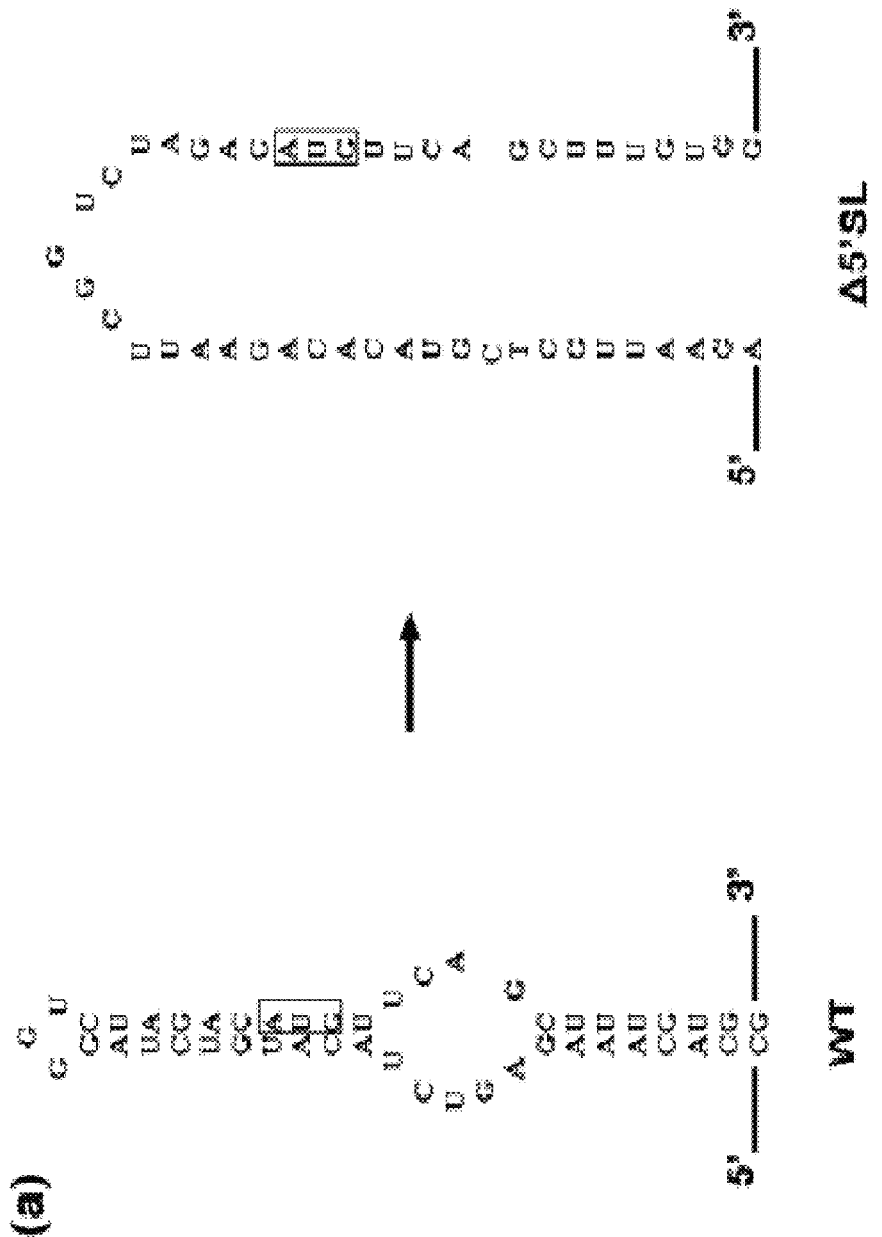
FIG. 7. 5'SL regulates myosindependent collagen secretion. (a) 5'SL sequence of mouse collagen α1(I) mRNA (WT; SEQ ID NO:7) and the mutation used to create the α1(I) 5'SL knockin mouse (5'SL; SEQ ID NO:9). (b) Effect of ML-7 on collagen secretion is dependent on 5'SL. Western blot analysis of cellular proteins (lanes 1 and 2) and medium proteins (lanes 3 and 4) from WT MEFs treated with ML-7 (lanes 1 and 3) and from untreated control WT MEFs (lanes 2 and 4). COL1A1, collagen α1(I) polypeptide; FIB, fibronectin as loading control. Lanes 5.8, the same experiment with Δ5'SL mutant MEFs.
Figure 7B:
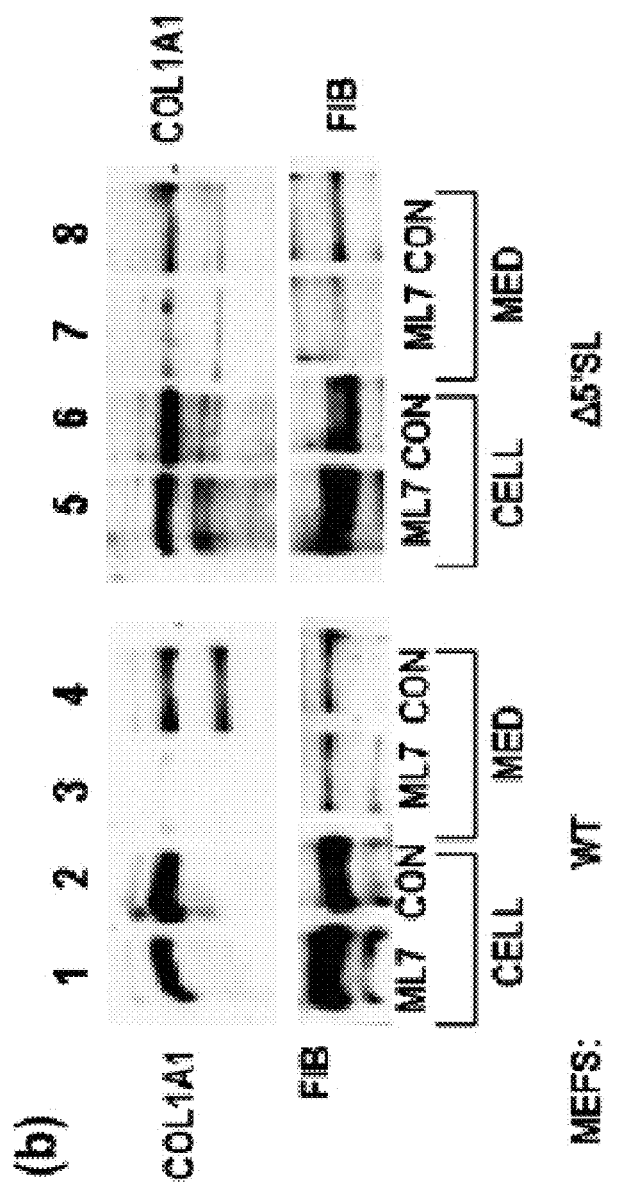

To investigate the role of the conserved 5'SL of collagen mRNAs in the regulation of their translation, we obtained mouse embryonic fibroblasts (MEFs) from mice in which 5'SL was disrupted in the context of the endogenous collagen α1(I) gene (Parsons et al., submitted). The mutation of 5'SL did not change the coding region of the α1(I) gene (FIG. 7a), and the 5'SL of the α2(I) gene was not changed. We then treated the MEFs with ML-7 and estimated the effect on collagen α1(I) polypeptide level intracellularly and in the medium (FIG. 7b). In wild-type (WT) MEFs, ML-7 treatment did not change the cellular level of α1(I) polypeptide (lanes 1 and 2); however, its secretion into the medium was drastically reduced (lanes 3 and 4). This result is similar to the result obtained with scleroderma fibroblasts (FIG. 3e). In Δ5'SL MEFs, treatment with ML-7 did not affect the secretion of α1(I) polypeptide; similar amounts were found in the medium of cells treated with ML-7 and in the medium of untreated cells (FIG. 7b, lanes 7 and 8). In these experiments, we could not measure the expression of collagen α2(I) polypeptide because the antibody poorly recognized the rodent polypeptide. Nevertheless, this result indicates that ML-7 treatment affects the secretion of collagen polypeptides only if it is encoded with 5'SL by the mRNA.

Involvement of Nonmuscle Myosin in Translation of Collagen mRNAs

To assess how the mutation of 5'SL in α1(I) mRNA affects the association of α1(I) and α2(I) mRNAs with nonmuscle myosin, we first analyzed their ability to bind LARP6. FIG. 8a shows that WT and Δ5'SL MEFs have comparable steady-state levels of collagen α2(I) mRNA, but Δ5'SL MEFs have 50% less collagen α1(I) mRNA (lane 2). This is due to the mutation of 5'SL, which destabilized this mRNA. We then expressed HA-tagged LARP6 in WT and Δ5'SL MEFs and performed immunoprecipitation with anti-HA antibody, followed by reverse transcription (RT) PCR analysis of collagen mRNAs in the immunoprecipitated material (FIG. 8b). In WT MEFs, both collagen mRNAs were pulled down with LARP6 (lane 1), while in Δ5'SL MEFs, only collagen α2(I) mRNA was pulled down (lane 2). This was expected, since 5'SL was mutated only in α1(I) mRNA. Fibronectin mRNA was not pulled down in either cell type. This verified that LARP6 interacts with 5'SL in vivo. When we performed the pulldown with anti-myosin IIB antibody from WT MEFs, both collagen mRNAs were found in the immunoprecipitate (FIG. 8c, lane 1). In Δ5'SL MEFs, collagen α1(I) mRNA was not associated with myosin IIB (lane 2), indicating that intact 5'SL is needed for this association. Unexpectedly, the α2(I) mRNA, which had the WT 5'SL and interacted with LARP6, was also not pulled down with myosin IIB (FIG. 8c, lane 2). This suggests that α2(I) mRNA cannot associate with nonmuscle myosin independently of α1(I) mRNA and that intact 5'SL on α1(I) mRNA is needed for binding both mRNAs to the myosin. We could not test if the opposite is true because MEFs with mutation of collagen α2(I) 5'SL are not available.

One of the roles of nonmuscle myosin filaments may be to present collagen mRNAs to ribosomes. Therefore, we assessed if the association of collagen mRNAs with nonmuscle myosin is dependent on intact polysomes. To show that collagen mRNAs specifically associate with nonmuscle myosin, we performed immunoprecipitations with anti-myosin-IIB-specific antibody and anti-calnexin antibody, as well as analysis of the pull-down of collagen mRNAs (FIG. 9a). Only the anti-myosin antibody immunoprecipitated collagen α1(I) and α2(I) mRNAs (lane 1). We then immunoprecipitated nonmuscle myosin from lung fibroblasts treated with cycloheximide or puromycin and analyzed if this can change the pull-down of collagen mRNAs. As control, the association with vimentin was analyzed in the same samples (FIG. 9b). In cycloheximide-treated cells, both collagen mRNAs were pulled down with nonmuscle myosin IIB (lane 1); however, when the cells were treated with puromycin, the great majority of these mRNAs were absent in the immunoprecipitate (lane 2). The treatment did not change the total level of nonmuscle myosin (FIG. 9c), suggesting that dissociation of polysomes decreased the association of collagen mRNAs with nonmuscle myosin. The association of collagen mRNAs with vimentin increased after the dissociation of polysomes (lanes 3 and 4). Puromycin treatment decreased the interaction of LARP6 and nonmuscle myosin and increased its interaction with vimentin (FIG. 9d). From these experiments, we concluded that the association of collagen mRNAs with nonmuscle myosin is favored when polysomes are intact, while collagen mRNAs preferentially bind vimentin filaments when polysomes are dissociated. To assess if nonmuscle myosin copurifies with polysomes, we fractionated polysomes on sucrose gradients[16] and analyzed for the presence of nonmuscle myosin in the fractions using Western blot analysis (FIG. 9f). To confirm which fractions represent polysomes, we compared the distributions of the ribosomal RNAs of cells treated with puromycin and cycloheximide (FIG. 9e). This analysis revealed that fractions 1-11 are puromycin sensitive and represent polysomes, while fractions 12-17 contained ribosomes and ribosomal subunits. Nonmuscle myosin was found in all polysomal fractions, as well as in nonpolysomal fractions and postpolysomal supernatants (FIG. 9f, top). When polysomes were dissociated, some nonmuscle myosin was lost, mostly from fractions 1-10. Puromycin did not change the total level of nonmuscle myosin, which was comparable to that of cycloheximide-treated cells; subsequent analysis confirmed that it was retained in the insoluble material, which was removed during the preparation of the polysomal lysate. When the cells were treated with ML-7, there was a decrease in the amount of nonmuscle myosin in the heaviest fractions containing polysomes (fractions 1-11, lower panel). ML-7 did not have an effect on the overall distribution of polysomes. We concluded that a fraction of nonmuscle myosin is associated with polysomes and that there is a correlation between the association of nonmuscle myosin with polysomes and the ability of cells to secrete type I collagen.

Figure 10:
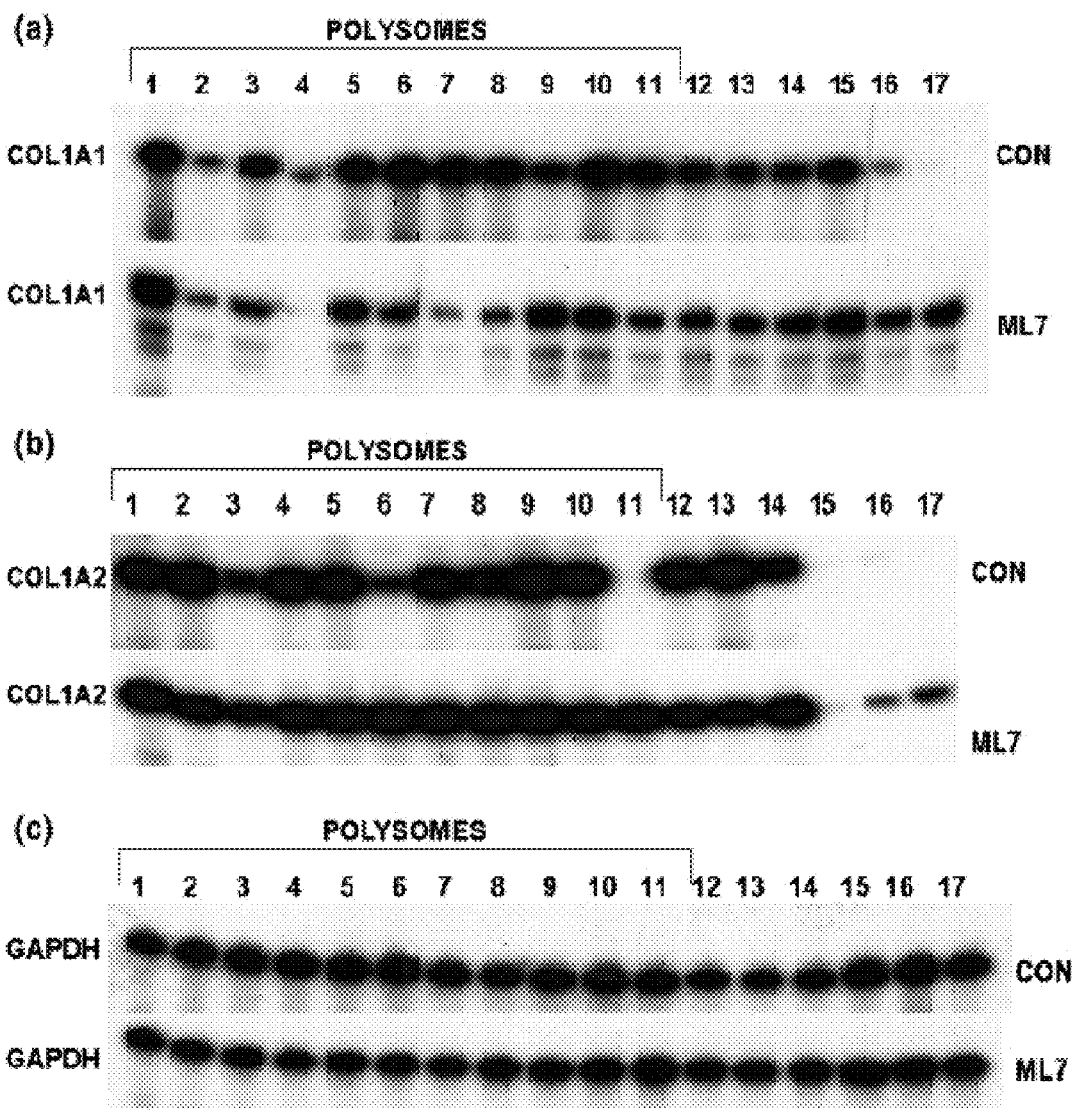
FIG. 10 The effect of ML-7 on the distribution of collagen mRNAs in polysomal fractions. (a) Distribution of collagen α1(I) mRNA on polysomes. Polysomes from control cells (CON) and ML-7-treated cells (ML-7) were fractionated as in FIG. 9e, and the fractions were analyzed by RT-PCR for the presence of collagen α1(I) mRNA (COL1A1). (b) Same experiment as in (a), except that collagen α2(I) mRNA was analyzed (COL1A2). (c) Analysis of glyceraldehyde-3-phosphate dehydrogenase mRNA in the fractions.

Collagen mRNAs can be clearly translated in the absence of nonmuscle myosin filaments. This is indicated by the fact that collagen α1(I) and α2(I) polypeptides were present intracellularly after ML-7 treatment, as well as after overexpression of KDMLCK (FIG. 3). Since polysomes can form on collagen mRNAs without the participation of nonmuscle myosin, we surmised that the effect of ML-7 on the polysomal profile of collagen mRNAs will be masked by this default translation. Nevertheless, FIG. 10 shows that after ML-7 treatment, a small fraction of collagen α1(I) and α2(I) mRNAs were shifted into nonpolysomal fractions 16 and 17. The total level of collagen mRNAs, as the sum of all fractions, was not significantly affected by ML-7 treatment. This indicates that there is a subset of polysomes involved in the translation of collagen mRNAs, the assembly of which is dependent on the integrity of nonmuscle myosin filaments.

Discussion

In heart fibrosis, reexpression of the fetal form of nonmuscle myosin was found only at the sites of focal fibrosis.[39] Mice that have the mutated 5'SL in the endogenous collagen α1(I) gene (and from which Δ5'SL MEFs used in this study were derived) develop 50% less liver fibrosis than control mice (Parsons et al., submitted for publication). These findings suggest that the mechanism involving 5'SL and nonmuscle myosin is important for high-level collagen synthesis in vivo. Therefore, the results described here are highly relevant to the regulation of collagen expression in fibrosis and the development of anti-fibrotic drugs.

Nonmuscle myosin has classically been implicated in promoting cell contractility, motility, and karyokinesis.[40,42] During states of high collagen demand, such as wound healing or fibrosis, there is activation and migration of fibroblasts to the site of insult. To enable motility, activated fibroblasts and myofibroblasts upregulate nonmuscle myosin expression.[43,44] Our results indicate for the first time that nonmuscle myosin filaments are also a prerequisite for the secretion of type I collagen, which commences after the arrival of the cells to the wound. Thus, motility and the ability to make type I collagen are integrated processes of collagen-producing cells.

Most human tissues synthesize exclusively the heterotrimer of type I collagen, although homotrimers of α1(I) chains readily form in the absence of α2(I) chains.[19,20] Thus, the cells have the ability to fold and secrete the homotrimer of type I collagen; however, there must be a mechanism that normally prevents this. If the translation of individual collagen chains is random and their registration and folding are not strictly coordinated, the formation of homotrimers would inevitably happen to a significant extent. One way to ensure the predominant synthesis of the heterotrimer would be to prevent the independent translation of α1(I) mRNA and to couple it to that of α2(I) mRNA. We have shown, in the prior filed provisional application incorporated herein by reference, that LARP6 is the protein that specifically binds the 5'SL of collagen α1(I) and α2(I) mRNAs.[16] The binding of LARP6 is of high affinity to prevent translation, suggesting that one of the roles of LARP6 may be to prevent the random translation of collagen mRNAs. There has been no other report on the involvement of nonmuscle myosin in translation. Here we show the following: (1) LARP6 associates collagen mRNAs with filaments composed of nonmuscle myosin; (2) disruption of nonmuscle myosin filaments results in either lack of secretion of collagen α2(I) polypeptide or diminished secretion of both α1(I) and α2(I) polypeptides and their increased intracellular degradation; (3) subcellular colocalization of collagen α1(I) and α2(I) polypeptides is diminished when myosin filaments are disrupted; (4) the function of nonmuscle myosin is dependent on the presence of 5'SL in collagen mRNAs; and (5) nonmuscle myosin associates with polysomes, and there is a subset of polysomes involved in the translation of collagen mRNAs that is dependent on the integrity of nonmuscle myosin filaments.

In the absence of the filaments, collagen polypeptides seem to be synthesized randomly, fail to fold into the heterotrimer, and are subjected to intracellular degradation. The secretion of α1(I) polypeptide was observed in lung fibroblasts treated with ML-7 and was diminished in scleroderma fibroblasts. Since α1(I) polypeptide has the propensity to form homotrimers,[19,20] it seems likely that, in the absence of myosin filaments, lung fibroblasts can compensate for and secrete the homotrimers, while scleroderma fibroblasts cannot. Nevertheless, in both cell types, increased intracellular degradation of α1(I) polypeptide also became apparent upon inhibition of the proteosome (FIG. 3f), suggesting that even the synthesis of collagen homotrimers is inefficient. Thus, nonmuscle myosin filaments are critical for coordinating the translation and folding of collagen polypeptides, possibly representing the mechanism that ensures the preferential synthesis of the heterotrimer of type I collagen.

Collagen α1(I) and α2(I) polypeptides show strict colocalization in the lumen of the ER; however, without nonmuscle myosin filaments, this colocalization cannot be maintained (FIG. 5a). At the same time, collagen polypeptides are subjected to accelerated intracellular degradation (FIG. 3f), which prevents their excessive accumulation in the cell. Our results indicate that the function of myosin in collagen synthesis may not be entirely dependent on the integrity of actin filaments. While disruption of nonmuscle myosin specifically affected collagen secretion, disruption of actin filaments in lung fibroblasts diminished the secretion of fibronectin as well and had only a minimal effect on collagen secretion in scleroderma fibroblasts (FIG. 6c).

Figure 2:
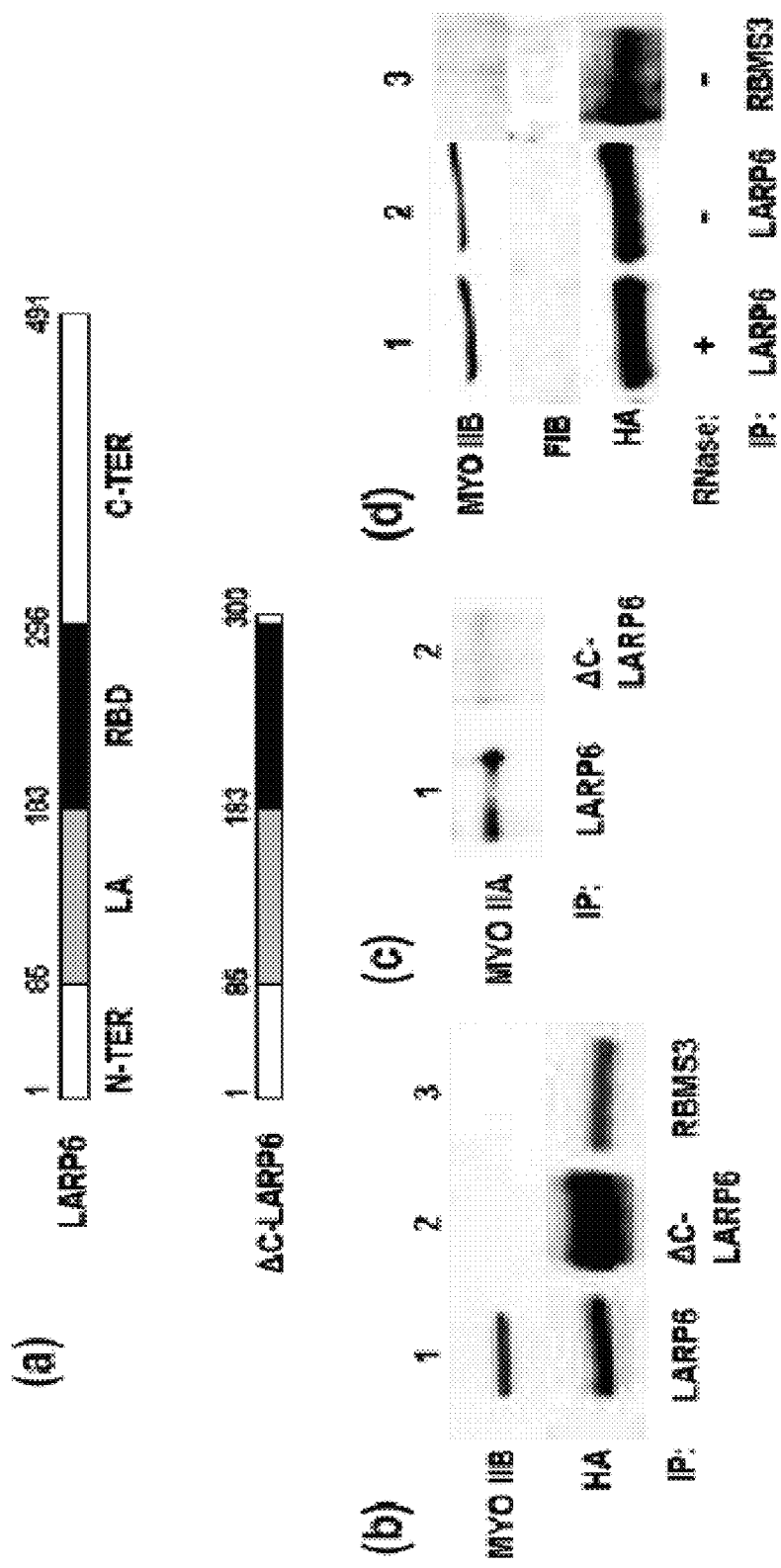
FIG. 2 shows the interaction of LARP6 with nonmuscle myosin; (a) schematic representation of the domains of LARP6; the Nterminal domain (N-TER), La homology domain (LA), RNA binding domain (RBD), and C-terminal domain (C-TER) are shown with amino acid numbering on top; ΔC-LARP6, C-terminal deletion mutant of LARP6; (b) immunoprecipitation of LARP6 and nonmuscle myosin; HA-tagged LARP6 (lane 1), HA-tagged ΔC-LARP6 (lane 2), and HA-tagged RBMS3 (lane 3) were expressed in human lung fibroblasts and immunoprecipitated with anti-HA antibody, and the immunoprecipitated material was analyzed by Western blot analysis using anti-myosin IIB antibody (MYO IIB). HA, Western blot analysis using anti-HA antibody as control for immunoprecipitation efficiency of the tagged proteins. (c) Experiment as in (b), but Western blot analysis was performed using anti-myosin IIA antibody (MYO IIA). (d) Interaction of LARP6 and nonmuscle myosin does not depend on the integrity of RNA. Experiment as in (b), but the lysate was treated with Rnase. A prior to immunoprecipitation (lane 1) or was not treated (lanes 2 and 3). The immunoprecipitate was analyzed with anti-myosin IIB antibody (MYO IIB), anti-fibronectin antibody (FIB; as control for specificity), and anti-HA antibody (HA; as control for precipitation efficiency).

The function of myosin filaments in collagen secretion is dependent on the presence of 5'SL in collagen mRNA. When 5'SL was mutated in the endogenous collagen α1(I) gene, the cells secreted α1(I) polypeptides regardless of the integrity of nonmuscle myosin filaments; however, when the polypeptides were encoded by mRNA with 5'SL, their secretion was dependent on nonmusclemyosin filaments (FIG. 7b). This clearly indicates that the association of collagen mRNAs with the nonmuscle myosin filaments, by binding of LARP6 to 5'SL, is needed for proper folding and secretion of type I collagen.[11] The additional band seen in lane 4 of FIG. 7b probably represents the mature collagen, processed by cleavage of the N-terminal and C-terminal domains of procollagen. LARP6 and nonmuscle myosin interact through the C-terminal domain of LARP6 (FIG. 2). Nonmuscle myosin does not bind collagen mRNAs directly, and since LARP6 is the only protein that binds 5'SL with high affinity,[16] it is almost certain that 5'SL associates collagen mRNAs with nonmuscle myosin through LARP6.

Figure 8:
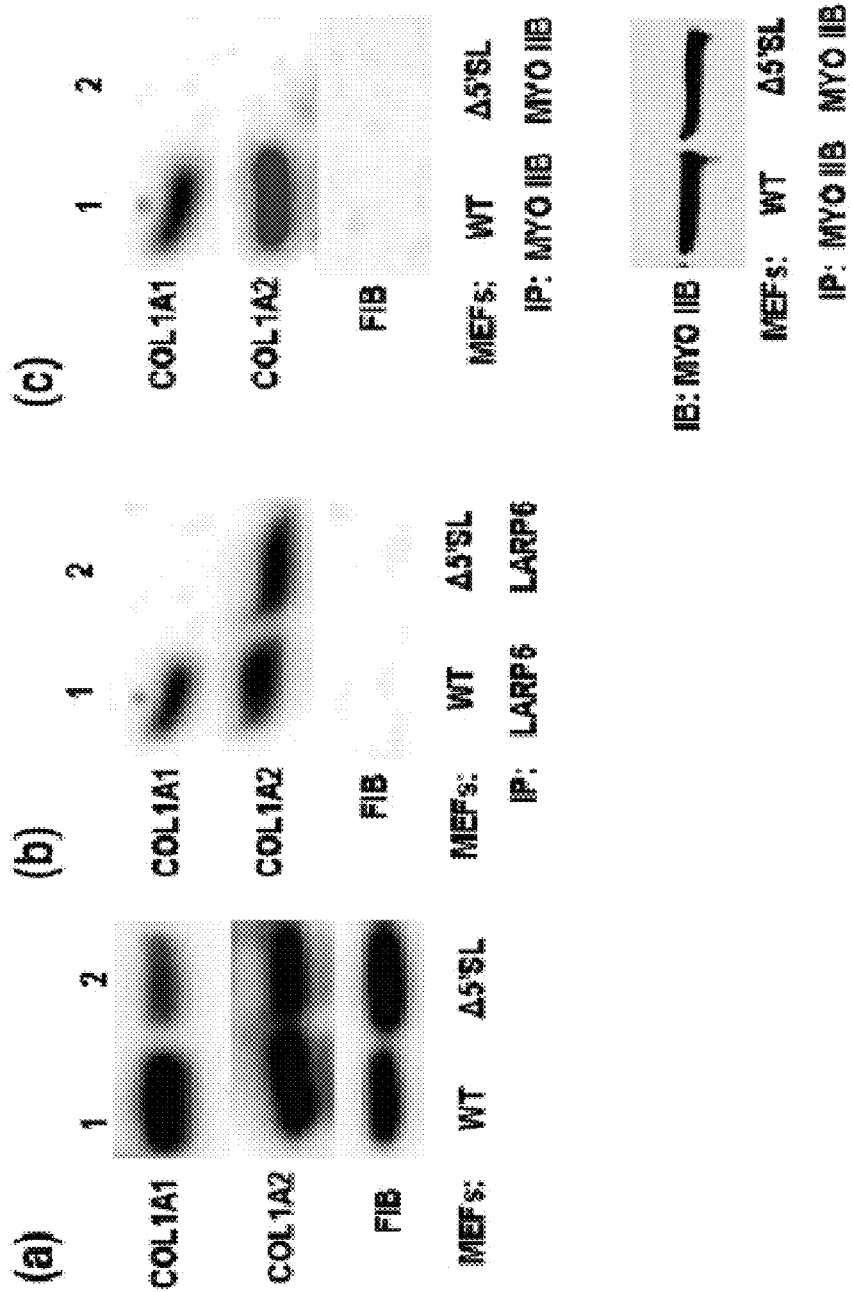
FIG. 8. Association of collagen α1(I) and α2(I) mRNAs with nonmuscle myosin. (a) Expression of collagen mRNAs in WT and Δ5'SL mutant MEFs. RT-PCR with total RNA from WT MEFs (lane 1) and Δ5'SL mutant MEFs (lane 2), and primers specific for collagen α1(I) mRNA (COL1A1), collagen α2(I) mRNA (COL1A2), and fibronectin mRNA (FIB) as loading control. (b) Coprecipitation of collagen mRNAs with LARP6. HA-tagged LARP6 was expressed in WT MEFs (lane 1) and Δ5'SL mutant MEFs (lane 2), and immunoprecipitated with anti-HA antibody. Immunoprecipitate was analyzed by RT-PCR as in (a). (c) Coprecipitation of collagen mRNAs with nonmuscle myosin. Immunoprecipitation with anti-myosin IIB antibody from extracts of WT MEFs (lane 1) and Δ5'SL mutant MEFs (lane 2). Immunoprecipitate was analyzed by RT-PCR as in (a). Bottom: Control Western blot analysis for equal pull-down of myosin IIB.

There have been no other reports indicating that nonmuscle myosin can regulate the translation of specific mRNAs. Our evidence that nonmuscle myosin participates in the translation of collagen mRNAs is indirect and based on the following: (1) a substantial amount of nonmuscle myosin copurifies with polysomes; (2) disruption of the filaments reduces the amount of nonmuscle myosin found in polysomal fractions (FIG. 9f); (3) dissociation of polysomes results in redistribution of collagen mRNAs from myosin filaments to vimentin filaments (FIG. 9b); (4) the strict subcellular colocalization of collagen α1(I) and α2(I) polypeptides is diminished if the filaments are disrupted (FIG. 5a); and (5) there is a subset of polysomes that translate collagen mRNAs in a myosin-dependent manner (FIG. 10). A dramatic change in the polysomal profile of collagen mRNAs upon treatment with ML-7 was not found because collagen mRNAs can be translated in the absence of 5'SL (FIG. 7b) and nonmuscle myosin filaments (FIG. 3). However, this results in the synthesis of homotrimer. LARP6 can form dimers, raising the possibility that it can organize collagen mRNAs into ribonucleoprotein particles containing multiple collagen mRNAs (manuscript in preparation). Collagen α2(I) mRNA does not bind nonmuscle myosin if 5'SL is mutated in α1(I) mRNA (FIG. 8). This indicates that there is some cross-talk between the two mRNAs through LARP6 and 5'SL, and that they may bind as a complex to the nonmuscle myosin filaments. Electron microscopy of the isolated polysomes containing collagen mRNAs showed that chain insertion into the ER lumen is coordinated. Coordinated translation of the signal peptides of collagen α1(I) and α2(I) chains may commence while these particles are still associated with the nonmuscle myosin filaments. Then, the signal recognition particle may target nascent chains to the membrane of the ER for cotranslational insertion into the lumen and folding, which start from the C-terminus of the chains.[46] To achieve this, the cell must integrate three processes: (1) cytoplasmic organization of collagen mRNAs, involving collagen mRNAs, LARP6, and nonmuscle myosin;[16] (2) translation elongation events on the membrane of the ER, involving signal recognition particle, translocons, and TRAM2;[12] and (3) protein folding events in the lumen of the ER, involving molecular chaperones and collagen-modifying enzymes.[47]

In conclusion, we have shown that LARP6 and nonmuscle myosin-dependent mechanism are required for the synthesis of a normal heterotrimeric type I collagen. We postulate that synthesis of type I collagen requires coordination of the translation of collagen α1(I) and α2(I) mRNAs. This is initiated by the binding of LARP6 to 5'SL and the interaction of LARP6 with nonmuscle myosin. Nonmuscle myosin filaments coordinate the translation of collagen α1(I) and α2(I) polypeptides, which favors the productive folding of the α1(I)-α2(I)-α1(I) heterotrimer of type I collagen. This mechanism seems to be active in fibrosis, raising the possibility that targeting binding of LARP6 to collagen mRNAs or nonmuscle myosin may lead to specific anti-fibrotic drugs.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

REFERENCES

1. Kivirikko, K. I. (1998). Collagen biosynthesis: a minireview cluster. Matrix Biol. 16, 355-356.
2. Friedman, S. L. (1999). Cytokines and fibrogenesis. Semin. Liver Dis. 19, 129-140.
3. Tsukada, S., Parsons, C. J. & Rippe, R. A. (2006). Mechanisms of liver fibrosis. Clin. Chim. Acta, 364, 33-60.
4. Leask, A., Denton, C. P. & Abraham, D. J. (2004). Insights into the molecular mechanism of chronic fibrosis: the role of connective tissue growth factor in scleroderma. J. Invest. Dermatol. 122.
5. Matsusaka, T., Katori, H., Homma, T. & Ichikawa, I. (1999). Mechanism of cardiac fibrosis by angiotensin. New insight revealed by genetic engineering. Trends Cardiovasc. Med. 9, 180-184.
6. Bitterman, P. B. & Henke, C. A. (1991). Fibroproliferative disorders. Chest, 99, 81S-84S.
7. Friedman, S. L. & Bansal, M. B. (2006). Reversal of hepatic fibrosis.fact or fantasy? Hepatology, 43, 582-S88.
8. Stefanovic, B., Hellerbrand, C., Holcik, M., Briendl, M., Aliebhaber, S. & Brenner, D. A. (1997). Posttranscriptional regulation of collagen alpha1(I) mRNA in hepatic stellate cells. Mol. Cell. Biol. 17, 5201-5209.

9. Eckes, B., Mauch, C., Huppe, G. & Krieg, T. (1996). Differential regulation of transcription and transcript stability of pro-alpha 1(I) collagen and fibronectin in activated fibroblasts derived from patients with systemic scleroderma. Biochem. J. 315, 549-554.

10. Mauch, C., Kozlowska, E., Eckes, B. & Krieg, T. (1992). Itered regulation of collagen metabolism in scleroderma fibroblasts grown within three-dimensional collagen gels. Exp. Dermatol. 1, 185-190.

11. Stefanovic, B. & Brenner, D. A. (2003). 5' Stem-loop of collagen alpha 1(I) mRNA inhibits translation in vitro but is required for triple helical collagen synthesis in vivo. J. Biol. Chem. 278, 927-933.

12. Stefanovic, B., Stefanovic, L., Schnabl, B., Bataller, R. & Brenner, D. A. (2004). TRAM2 protein interacts with endoplasmic reticulum Ca2+ pump Serca2b and is necessary for collagen type I synthesis. Mol. Cell. Biol. 24, 1758-1768.

13. Lindquist, J. N., Kauschke, S. G., Stefanovic, B., Burchardt, E. R. & Brenner, D. A. (2000). Characterization of the interaction between alphaCP(2) and the 3' untranslated region of collagen alpha1(I) mRNA. Nucleic Acids Res. 28, 4306-4316.

14. Stefanovic, B., Hellerbrand, C. & Brenner, D. A. (1999). Regulatory role of the conserved stem loop structure at the 5' end of collagen alpha1(I) mRNA. Mol. Cell. Biol. 19, 4334-4342.

15. Stefanovic, B., Lindquist, J. & Brenner, D. A. (2000). The 5' stem-loop regulates expression of collagen alpha1(I) mRNA in mouse fibroblasts cultured in a three-dimensional matrix. Nucleic Acids Res. 28, 641-647.

16. Cai, L., Fritz, D., Stefanovic, L. & Stefanovic, B. (2009). Binding of LARP6 to the conserved 5' stem-loop regulates translation of mRNAs encoding type I collagen. J. Mol. Biol. 395, 309-326.

17. Cai, L., Fritz, D., Stefanovic, L. & Stefanovic, B. (2009). Coming together: liver fibrosis, collagen mRNAs and the RNA binding protein. Expert Rev. Gastroenterol. Hepatol. 3, 1-3.

18. Uitto, J. (1979). Collagen polymorphism: isolation and partial characterization of alpha 1(I)-trimer molecules in normal human skin. Arch. Biochem. Biophys. 192, 371-379.

19. Malfait, F., Symoens, S., Coucke, P., Nunes, L., De Almeida, S. & De Paepe, A. (2006). Total absence of the alpha2(I) chain of collagen type I causes a rare form of Ehlers.Danlos syndrome with hypermobility and propensity to cardiac valvular problems. J. Med. Genet. 43, e36.

20. Sims, T. J., Miles, C. A., Bailey, A. J. & Camacho, N. P. (2003). Properties of collagen in OIM mouse tissues. Connect. Tissue Res. 44, 202-205.

21. Beck, K., Boswell, B. A., Ridgway, C. C. & Bachinger, H. P. (1996). Triple helix formation of procollagen type I can occur at the rough endoplasmic reticulum membrane. J. Biol. Chem. 271, 21566-21573.

22. Lamande, S. R. & Bateman, J. F. (1999). Procollagen folding and assembly: the role of endoplasmic reticulum enzymes and molecular chaperones. Semin. Cell Dev. Biol. 10, 455-464.

23. Pace, J. M., Wiese, M., Drenguis, A. S., Kuznetsova, N., Leikin, S., Schwarze, U. et al. (2008). Defective C-propeptides of the proalpha2(I) chain of type I procollagen impede molecular assembly and result Myosin-Dependent Collagen Synthesis 577 in osteogenesis imperfecta. J. Biol. Chem. 283, 16061-16067.

24. Hartmuth, K., Urlaub, H., Vornlocher, H. P., Will, C. L., Gentzel, M., Wilm, M. & Luhrmann, R. (2002). Protein composition of human prespliceosomes isolated by a tobramycin affinity-selection method. Proc. Natl. Acad. Sci. USA, 99, 16719-16724.

25. Hartmuth, K., Vornlocher, H. P. & Luhrmann, R. (2004). Tobramycin affinity tag purification of spliceosomes. Methods Mol. Biol. 257, 47-64.

26. Wolin, S. L. & Cedervall, T. (2002). The La protein. Annu. Rev. Biochem. 71, 375-403.

27. Fritz, D. & Stefanovic, B. (2007). RNA-binding protein RBMS3 is expressed in activated hepatic stellate cells and liver fibrosis and increases expression of transcription factor Prx1. J. Mol. Biol. 371, 585-595.

28. Bain, J., McLauchlan, H., Elliott, M. & Cohen, P. (2003). The specificities of protein kinase inhibitors: an update. Biochem. J. 371, 199-204.

29. Connell, L. E. & Helfman, D. M. (2006). Myosin light chain kinase plays a role in the regulation of epithelial cell survival. J. Cell Sci. 119, 2269-2281.

30. Takizawa, N., Ikebe, R., Ikebe, M. & Luna, E. J. (2007). Supervillin slows cell spreading by facilitating myosin II activation at the cell periphery. J. Cell Sci. 120, 3792-3803.

31. Stefanovic, B., Schnabl, B. & Brenner, D. A. (2002). Inhibition of collagen alpha 1(I) expression by the 5' stem-loop as a molecular decoy. J. Biol. Chem. 277, 18229-18237.

32. Adesida, A. B., Grady, L. M., Khan, W. S. & Hardingham, T. E. (2006). The matrix-forming phenotype of cultured human meniscus cells is enhanced after culture with fibroblast growth factor 2 and is further stimulated by hypoxia. Arthritis Res. Ther. 8, R61.

33. Rieske, P., Krynska, B. & Azizi, S. A. (2005). Human fibroblast-derived cell lines have characteristics of embryonic stem cells and cells of neuro-ectodermal origin. Differentiation, 73, 474-483.

34. Oliver, J. E., Thompson, E. M., Pope, F. M. & Nicholls, A. C. (1996). Mutation in the carboxy-terminal propeptide of the Pro alpha 1(I) chain of type I collagen in a child with severe osteogenesis imperfecta (OI type III): possible implications for protein folding. Hum. Mutat. 7, 318-326.

35. Allingham, J. S., Smith, R. & Rayment, I. (2005). The structural basis of blebbistatin inhibition and specificity for myosin II. Nat. Struct. Mol. Biol. 12, 378-379.

36. Kovacs, M., Toth, J., Hetenyi, C., Malnasi-Csizmadia, A. & Sellers, J. R. (2004). Mechanism of blebbistatin inhibition of myosin II. J. Biol. Chem. 279, 35557-35563.

37. Limouze, J., Straight, A. F., Mitchison, T. & Sellers, J. R. (2004). Specificity of blebbistatin, an inhibitor of myosin II. J. Muscle Res. Cell Motil. 25, 337-341.

38. Dancker, P. & Low, I. (1979). Complex influence of cytochalasin B on actin polymerization. Z. Naturforsch. C, 34, 555-557.

39. Pandya, K., Kim, H. S. & Smithies, O. (2006). Fibrosis, not cell size, delineates beta-myosin heavy chain reexpression during cardiac hypertrophy and normal aging in vivo. Proc. Natl. Acad. Sci. USA, 103, 16864-16869.

40. Lofgren, M., Ekblad, E., Morano, I. & Arner, A. (2003). Nonmuscle myosin motor of smooth muscle. J. Gen. Physiol. 121, 301-310.

41. Marini, M., Bruschi, M., Pecci, A., Romagnoli, R., Musante, L., Candiano, G. et al. (2006). Non-muscle myosin heavy chain IIA and IIB interact and colocalize in living cells: relevance for MYH9-related disease. Int. J. Mal. Med. 17, 729-736.

42. Simerly, C., Nowak, G., de Lanerolle, P. & Schatten, G. (1998). Differential expression and functions of cortical myosin IIA and IIB isotypes during meiotic maturation, fertilization, and mitosis in mouse oocytes and embryos. Mol. Biol. Cell, 9, 2509-2525.
43. Tangkijvanich, P., Tam, S. P. & Yee, H. F., Jr. (2001). Wound-induced migration of rat hepatic stellate cells is modulated by endothelin-1 through rho-kinasemediated alterations in the acto-myosin cytoskeleton. Hepatology, 33, 74-80.
44. Conrad, P. A., Giuliano, K. A., Fisher, G., Collins, K., Matsudaira, P. T. & Taylor, D. L. (1993). Relative distribution of actin, myosin I, and myosin II during the wound healing response of fibroblasts. J. Cell Biol. 120, 1381-1391.
45. Veis, A., Leibovich, S. J., Evans, J. & Kirk, T. Z. (1985). Supramolecular assemblies of mRNA direct the coordinated synthesis of type I procollagen chains. Proc. Natl. Acad. Sci. USA, 82, 3693-3697.
46. Khoshnoodi, J., Cartailler, J. P., Alvares, K., Veis, A. & Hudson, B. G. (2006). Molecular recognition in the assembly of collagens: terminal noncollagenous domains are key recognition modules in the formation of triple helical protomers. J. Biol. Chem. 281, 38117-38121.
47. Gura, T., Hu, G. & Veis, A. (1996). Posttranscriptional aspects of the biosynthesis of type 1 collagen proalpha chains: the effects of posttranslational modifications on synthesis pauses during elongation of the pro alpha 1 (I) chain. J. Cell. Biochem. 61, 194-215.
48. He, T. C., Zhou, S., da Costa, L. T., Yu, J., Kinzler, K. W. & Vogelstein, B. (1998). A simplified system for generating recombinant adenoviruses. Proc. Natl. Acad. Sci. USA, 95, 2509-2514.
49. Stefanovic, L., Brenner, D. A. & Stefanovic, B. (2005). Direct hepatotoxic effect of KC chemokine in the liver without infiltration of neutrophils. Exp. Biol. Med. (Maywood), 230, 573-586.
50. Stefanovic, L. & Stefanovic, B. (2006). Mechanism of direct hepatotoxic effect of KC chemokine: sequential activation of gene expression and progression from inflammation to necrosis. J. Interferon Cytokine Res. 26, 760-770.
51. Bradford, M. M. (1976). A rapid and sensitive method for the quantitation of microgram quantities of protein utilizing the principle of protein.dye binding. Anal. Biochem. 72, 248-254.

That which is claimed:

1. A method of testing an agent for the ability to interfere with collagen synthesis, the method comprising:
   reacting an isolated purified polypeptide having an amino acid sequence comprising SEQ ID NO: 1 with collagen mRNAs in the presence of the agent; and
   detecting whether the agent has interfered with binding of the polypeptide to the collagen mRNAs.

2. A method of testing an agent for the ability to interfere with collagen synthesis, the method comprising:
   reacting an isolated purified polypeptide having an amino acid sequence comprising SEQ ID NO: 1 with nonmuscle myosin filaments in the presence of the agent; and
   detecting whether the agent has interfered with binding of the polypeptide to the nonmuscle myosin filaments.

3. A method of screening an agent for the ability to interfere with collagen synthesis, the method comprising:
   reacting an isolated purified polypeptide having an amino acid sequence comprising SEQ ID NO: 1 with collagen mRNAs and nonmuscle myosin filaments in the presence of the agent; and
   detecting whether the agent has interfered with binding of the polypeptide to either or both the collagen mRNAs or the nonmuscle myosin filaments.

* * * * *